(12) United States Patent
Friedman et al.

(10) Patent No.: US 9,164,113 B2
(45) Date of Patent: Oct. 20, 2015

(54) METHODS, SYSTEMS, AND APPARATUS ADAPTED TO TRANSFER SAMPLE CONTAINERS

(75) Inventors: Glenn M. Friedman, Redding, CT (US); Erich Kling, Fishkill, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 664 days.

(21) Appl. No.: 13/389,320

(22) PCT Filed: Aug. 6, 2010

(86) PCT No.: PCT/US2010/044648
§ 371 (c)(1),
(2), (4) Date: Feb. 7, 2012

(87) PCT Pub. No.: WO2011/017586
PCT Pub. Date: Feb. 10, 2011

(65) Prior Publication Data
US 2012/0134769 A1    May 31, 2012

Related U.S. Application Data

(60) Provisional application No. 61/232,021, filed on Aug. 7, 2009.

(51) Int. Cl.
*B25J 9/04* (2006.01)
*G01N 35/00* (2006.01)
*B25J 15/02* (2006.01)
*G01N 35/04* (2006.01)

(52) U.S. Cl.
CPC ............. *G01N 35/0099* (2013.01); *B25J 9/041* (2013.01); *B25J 15/0253* (2013.01); *G01N 2035/0405* (2013.01)

(58) Field of Classification Search
CPC ............ B25J 9/041; B25J 9/042; B25J 9/043; B25J 9/1633; B25J 13/085; B25J 15/0038; B25J 15/0042; B25J 15/0066; B25J 15/0253; B25J 15/026; B25J 15/028; B25J 15/0286; B25J 15/0293; B25J 15/0608; B25J 15/0616; B25J 19/0091; G01N 35/0099; G01N 2035/04
USPC ........ 81/3.4; 294/81.62, 119.1, 207; 414/618, 414/624, 625, 627, 680, 687, 728, 729, 731, 414/736, 737, 738, 741, 744.1, 744.2, 414/744.3, 744.4, 744.5, 744.6, 744.7, 414/744.8, 749.1, 751.1; 422/63, 65
See application file for complete search history.

(56) References Cited

U.S. PATENT DOCUMENTS 4,522,089 A    6/1985    Alvi
(Continued)

FOREIGN PATENT DOCUMENTS

JP    Sho 63-034029 A    2/1988
JP    H0512118 B2    2/1993
(Continued)

OTHER PUBLICATIONS

English translation of Japanese Office Action dated Feb. 25, 2014 of corresponding Japanese Patent Application No. 2012-523970, 11 Pages.
English translation of Fig. 1 elements of Japanese Publication No. JPH0512118 (B2), 1 Page.

*Primary Examiner* — Saul Rodriguez
*Assistant Examiner* — Brendan Tighe
(74) *Attorney, Agent, or Firm* — Dugan & Dugan, PC

(57) ABSTRACT

A method adapted to transfer a sample container such as a capped sample tube is disclosed. In one aspect, the method includes gripping a sample tube body with a first gripper pair and a cap with a second gripper pair of a gripper apparatus. In another aspect, a seating member may contact the cap to aid in the positioning of the sample container. Apparatus and systems for carrying out the method are provided, as are other aspects.

21 Claims, 18 Drawing Sheets

(56) References Cited

U.S. PATENT DOCUMENTS 5,455,006 A * 10/1995 Aota et al. .................. 422/63
5,658,532 A *  8/1997 Kurosaki et al. ............ 422/64
6,586,255 B1 *  7/2003 Hubert et al. ............... 436/45

FOREIGN PATENT DOCUMENTS

| JP | Hei 5-065975 A | 3/1993 |
| JP | Hei 8-243969 A | 9/1996 |
| JP | 2009-006460 A | 1/2009 |

* cited by examiner

METHODS, SYSTEMS, AND APPARATUS ADAPTED TO TRANSFER SAMPLE CONTAINERS

RELATED APPLICATIONS

The present application claims priority to U.S. Provisional Patent Application No. 61/232,021 filed Aug. 7, 2009, and entitled "Robotic Tube Transport System", the disclosure of which is hereby incorporated herein by reference in its entirety for all purposes.

FIELD OF THE INVENTION

The present invention relates generally to methods, systems, and apparatus adapted for transferring sample containers (e.g., sample tubes) between locations.

BACKGROUND OF THE INVENTION

In testing within clinical laboratories to measure various chemical constituents in biological fluids obtained from patients, such as whole blood, blood serum, blood plasma, interstitial fluid, urine, and the like, automated clinical analyzers and other automated equipment (e.g., centrifuges) may reduce the number of trained technicians required to perform analyses or pre-analysis processing, improve overall accuracy, and reduce the cost per operation performed.

Typically, an automated analyzer or automated equipment for performing pre-analysis processing may include an automated system (e.g., a robot) that is adapted to automatically transfer sample containers (e.g., sample tubes) from one location to another.

During the transfer operation, a robot under the control of a robot controller, may position a pair of fingers in order to grip the sample container. During the transfer step, sometimes the tube may slip within the fingers, and, thus, may become improperly positioned for the next operation. Additionally, the location within the fingers may be unknown especially given that the sample containers may be from an assortment of sizes and types (i.e., have different width and/or length sample tube bodies and various configurations of caps). As such, the robot controller may either crash the sample container into a receptacle adapted to receive the sample container because the sample container is improperly positioned in the fingers, or otherwise allow it to be improperly inserted (e.g., not bottomed out) into a receptacle. Accordingly, the inventor recognized there is a need for a method of transferring sample containers that does not suffer from the aforementioned problems.

SUMMARY OF THE INVENTION

According to a first aspect, the present invention provides a gripper apparatus. The gripper apparatus includes a gripper component including a first and second moveable jaws arranged alongside of a gripper axis; a first finger coupled to the first moveable jaw; a second finger coupled to the second moveable jaw, the first and second fingers are adapted to grip a sample container; and a seating member positioned adjacent to the first and second fingers and moveable along the gripper axis, the seating member adapted to contact a cap of the sample container when the first and second fingers are in an opened configuration.

According to another aspect, the present invention provides a sample container transfer system. The system includes a robot apparatus moveable in at least one coordinate direction; and a gripper apparatus coupled to, and moveable by, the robot apparatus, the gripper apparatus including a gripper component including a first moveable jaw and second moveable jaw each arranged alongside of a gripper axis, a first finger coupled to the first moveable jaw, a second finger coupled to the second moveable jaw, the first finger and second finger are each adapted to grip a sample container, and a seating member positioned adjacent to the first finger and the second finger and moveable along the gripper axis, the seating member adapted to contact a cap of the sample container when the first and second fingers are in an opened configuration.

The present invention also provides a method of transferring a sample container. The method includes providing a gripper component including a first moveable jaw and a second moveable jaw each arranged alongside of a gripper axis; providing a first finger coupled to the first moveable jaw; providing a second finger coupled to the second moveable jaw; contacting a cap of the sample container with a seating member moveable along the gripper axis and positioned adjacent to the first and second fingers when the first and second fingers are in an opened configuration; and gripping the sample container with the first finger and the second finger.

According to another aspect, the present invention provides a gripper apparatus. The apparatus includes a first gripper component including a first moveable jaw and a second moveable jaw; a second gripper component including a third moveable jaw and fourth moveable jaw; a first finger coupled to the first moveable jaw; a second finger coupled to the second moveable jaw, wherein the first finger and the second finger are each arranged alongside of the gripper axis and are adapted to grip a sample tube body of a sample container; a third finger coupled to the third moveable jaw; and a fourth finger coupled to the fourth moveable jaw, wherein the third finger and the fourth finger are each arranged alongside of the gripper axis and are adapted to grip a cap of a sample container.

According to another aspect, the present invention provides a sample container transfer system. The system includes a robot apparatus adapted to be moveable in at least one coordinate direction; and a gripper apparatus coupled to and adapted to be moved by the robot apparatus, the gripper apparatus including a first gripper component including a first moveable jaw and a second moveable jaw each arranged alongside of a gripper axis, a second gripper component including a third moveable jaw and a fourth moveable jaw arranged alongside of the gripper axis, a first finger coupled to the first moveable jaw, a second finger coupled to the second moveable jaw, wherein the first finger and second finger are adapted to grip a sample tube body of a sample container, a third finger coupled to the third moveable jaw, and a fourth finger coupled to the fourth moveable jaw, wherein the third finger and the fourth finger are adapted to grip a cap of a sample container.

The present invention also provides a method of transferring a sample container. The method includes gripping a sample tube body of the sample container with a first pair of fingers of a gripper apparatus; gripping the cap of the sample container with a second pair of fingers of the gripper apparatus; and transferring the sample container being gripped by the gripper apparatus from a first location to a second location.

Still other aspects, features, and advantages of the present invention may be readily apparent from the following detailed description by illustrating a number of exemplary embodiments and implementations, including the best mode contemplated for carrying out the present invention. The present invention may also be capable of other and different embodiments, and its several details may be modified in various respects, all without departing from the spirit and scope of the present invention. Accordingly, the drawings and descriptions are to be regarded as illustrative in nature, and not as restrictive. The drawings are not necessarily drawn to scale. The invention is to cover all modifications, equivalents, and alternatives falling within the spirit and scope of the invention.

BRIEF DESCRIPTION OF THE DRAWINGS

The invention will be better understood by referring to the detailed description taken in conjunction with the following drawings.

DETAILED DESCRIPTION OF THE INVENTION

Figure 1A:
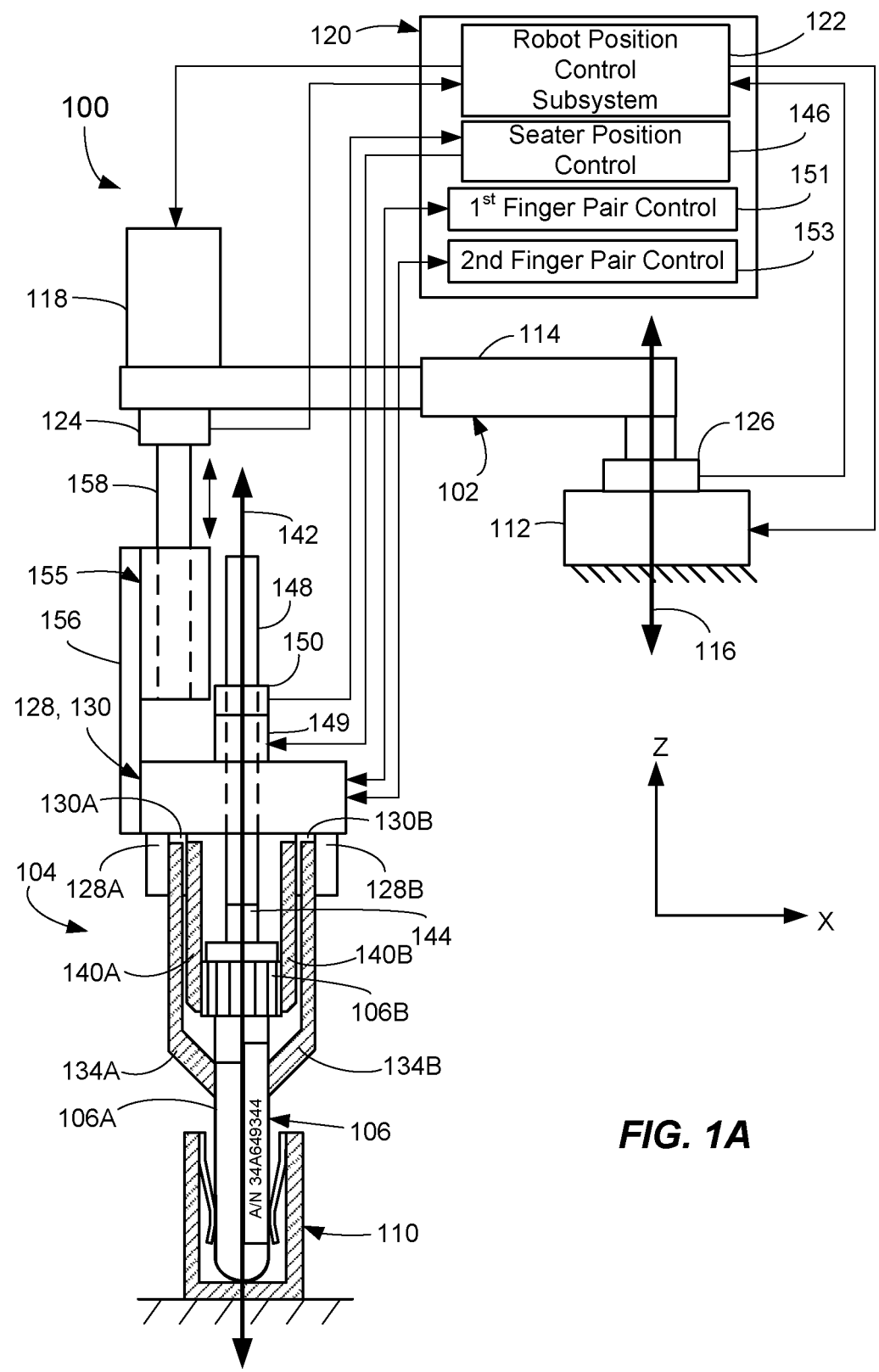
FIG. 1A is a partially cross-sectioned schematic side view diagram of a sample container transfer system according to aspects of the present invention.

In view of the foregoing difficulties, there is an unmet need to reduce the propensity for sample containers (e.g., sample tubes) to slip or be improperly grasped by the gripper apparatus in sample container transfer systems. Additionally, there is an unmet need to reduce the propensity for sample containers (e.g., sample tubes) to be improperly positioned within the gripper apparatus, or at a pick or place destination by the sample container transfer system. This may occur because the size (e.g., length and/or diameter) of the sample tube body and/or the configuration of the cap may vary considerably.

Accordingly, in one aspect, the sample container transfer system is provided that includes or consists of a gripper apparatus (e.g., a dual parallel-jaw gripper apparatus) mounted to a robot apparatus. The gripper components of the gripper apparatus may be mounted along a common gripper axis. Each of the gripper components may include fingers coupled thereto that are designed to grip a sample container having a sample tube body and a cap. A first set (pair) of fingers is adapted to grip the sample tube at a lower fixed position. A second set (pair) of fingers is adapted to grip the cap (e.g., the side of the cap). Accordingly, positive gripping of the sample container is provided regardless of the height or width of the sample tube body or shape or size of the cap. Both sets of fingers may compensate for large diameter or small diameter sample tube bodies and caps of various sizes and shapes.

In another exemplary embodiment, the gripper apparatus may include a seating member (e.g., a plunger) that may extend out towards an end of the fingers in a direction substantially parallel to the gripper axis. In particular, in some embodiments, the seating member may be retracted when the fingers are in an opened configuration, and may retract from the ends of the fingers when the fingers are in a closed configuration. In this manner, the seating member may be adapted to contact a top of the cap during a pick operation wherein a sample container is acquired from a location. The seating member (e.g., plunger) may retract (e.g., move up) when the fingers are in a closed configuration. In some instances (e.g., during a pick operation), the seating member may be allowed to substantially freely move up upon contact with the cap such that a position sensor coupled to the seating member may acquire position information about the location of the cap. In a like manner, the seating member (e.g., plunger) may act as a stripper to push a sample container out of the fingers when the fingers are in an opened configuration such as when the gripper apparatus is performing a place operation wherein the sample container is placed into a receptacle.

According to further embodiments, the gripper apparatus or sample container transfer system may include a vertical load limiting device (e.g., a linear clutch or crash slide). The vertical load limiting device may be mounted on or to the gripper apparatus or elsewhere between the robot apparatus and the gripper apparatus. The vertical load limiting device may function to detect collisions (via exceeding a preset load) and break away (e.g., along the Z-axis). This enables the gripper apparatus to stop its motion progression and thereby prevent overloading of pick or place destinations, the sample container (which may be glass), or the gripper apparatus and may prevent the gripper apparatus from further approaching such destinations wherein a crash may occur.

These and other aspects and features of the invention will be described with reference to FIGS. 1A-6 herein.

Figure 1B:
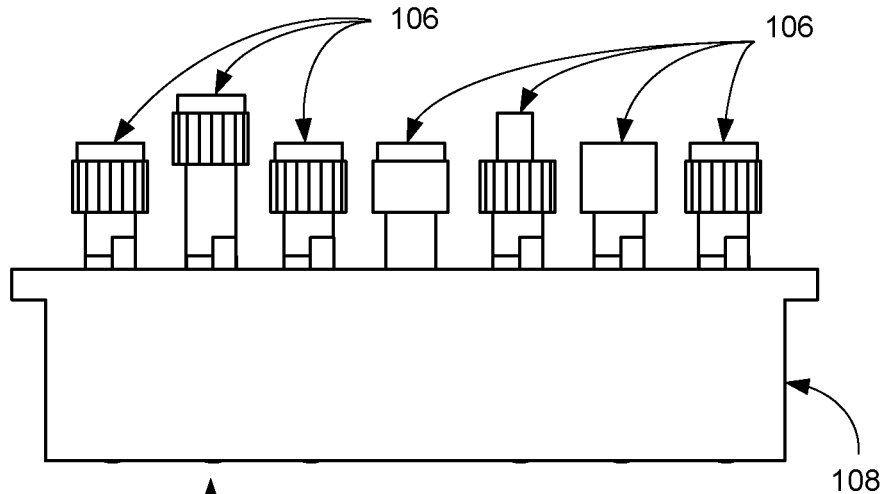
FIG. 1B is a schematic side view diagram of an exemplary sample rack.

Referring now to FIG. 1A, a sample container transfer system 100 is illustrated. The sample container transfer system 100 includes a robot apparatus 102 coupled to a gripper apparatus 104. Together, the robot apparatus 102 and the gripper apparatus 104 are adapted to grip a sample container 106 and carry out motion of the sample container 106 between a first location and a second location, for example. As shown in FIG. 1B, the first location may be at a sample rack 108 where one or more sample containers 106 are received and are awaiting processing, for example. The second location may be a location at a clinical analyzer, automated transport system, or other piece of equipment (e.g., pre-analysis processing equipment) where the specimen contained in the sample container 106 may undergo further processing or analysis. For example, the second location may be a receptacle 110 adapted to receive the sample container 106. The receptacle may be any size or shape and may be integrated into a clinical analyzer or piece of equipment. For example, the receptacle may be received in or part of a centrifuge.

The robot apparatus 102 may include any suitable type of robot for moving the gripper apparatus 104 in at least one coordinate direction. For example, in some embodiments, the robot apparatus may be a simple Z-axis robot with only Z-axis motion capability. In other embodiments, the robotic apparatus 102 may be an XZ-axis robot with only X-axis and Z-axis motion capability. In this version, the robotic apparatus 102 may pick a sample container 106 from one location, raise the gripper apparatus 104 in the Z-axis, travel along the X-axis direction, and then lower the gripper apparatus 104 to place a sample container 106 into a receptacle 110. In yet another embodiment, as is illustrated in FIG. 1A, the robotic apparatus 102 may be an XYZ-axis robot with X-axis, Y-axis, and Z-axis motion capability. In this manner, the robotic apparatus 102 may pick a sample container 106 from one location (e.g., from a sample container 108), raise and/or lower the gripper apparatus 104 in the Z-axis, travel along the X-axis direction and along the Y-axis direction (into and out of the paper in FIG. 1A), and then lower the gripper apparatus 104 to place the sample container 106 into a receptacle 110, for example.

The robot apparatus 102 may be a SCARA-type robot and may include a rotational motor 112 (e.g., a stepper motor) adapted to cause rotation of an arm assembly 114 about a fixed axis 116 to provide horizontal motion capability (in the X-axis and Y-axis directions), for example. The arm assembly 114 may include one or more arms that may telescope relative to one another, or otherwise move relative to one another. For example, in some embodiments, the arm assembly 114 may include a forearm component, an elbow component, and an upper arm component. Furthermore, vertical motion of the gripper apparatus 104 along a vertical Z-axis may be provided by any suitable type of linear actuator 118 (e.g., pneumatic, hydraulic, electrical, etc.) coupled between the arm assembly 114 and the gripper apparatus 104.

The motion of the rotational actuator 112 and linear actuator 118 may be controlled by a controller 120 adapted to execute all robot motions utilizing a robot position control subsystem 122. The position control subsystem 122 may control the motions according to a pre-established and programmed motion routine provided to accomplish the pick and place operations. Suitable position/rotation feedback may be provided to the robot position control subsystem 122 by sensors 124, 126 or other feedback components or systems. The control function performed by the controller 120 may be provided by any suitable computer, processor, or the like. The robotics and position control of the robot apparatus 102 is entirely conventional and will not be described further herein.

Various broad inventive aspects of the gripper apparatus 104 will now be described in detail with reference to FIGS. 1A-1E herein. Referring first FIG. 1A, the gripper apparatus 104 may, in one aspect, be adapted and operable to simultaneously grasp a sample container 106 by both the sample tube body 106A and the cap 106B. In this manner, excellent gripping action of the sample container 106 is provided, even when the sample tube body 106A and/or cap 106B may be quite variable in size from one sample container 106 to the next.

The ability to simultaneously grasp the tube body 106A and the cap 106B may be achieved by including a first gripper component 128 and a second gripper component 130. First and second gripper components 128, 130 may be arranged in a side-by-side configuration as shown in the FIG. 1D embodiment. The side-by-side configuration of the components 128, 130 is the same for the embodiment of FIGS. 1A and 1E. The gripper components 128, 130 may be parallel jaw grippers, such a two-jaw model DPDL series parallel gripper available from De-Sta-Co of Charlevoix, Mich. However, any suitable gripper component that includes moveable jaws may be used, such as parallel or even nonparallel moveable jaws. The gripper components 128, 130 may be electrically, pneumatically, or hydraulically driven to open and close the jaws. Moreover the invention may be adapted to chucking type, three-jaw gripper components.

In the depicted embodiment, opposing jaws 128A, 128B of the first gripper component 128 may be actuated to move a first finger 134A and a second finger 134B (a first finger pair) that are mechanically coupled to the jaws 128A, 128B such that they open and close along the directions indicated by arrows 135. Likewise, opposing jaws 130A, 130B of the second gripper component 130 may be mechanically coupled to third and fourth fingers 140A, 140B. The jaws 130A, 130B also be moveable to open and close along the directions indicated by arrows 137 to move (open and close) the third and fourth fingers 140A, 140B (a second finger pair) that are coupled to the jaws 130A, 130B. This results in the ability to independently control motion of the first and second fingers 134A, 134B and third and fourth fingers 140A, 140B. As such, the first pair of fingers 134A, 134B may be adapted to contact and grip the sample tube body 106A (e.g., on an upper portion thereof below cap 106B), and the second pair of fingers 140A, 140B may be adapted to contact and grip the cap 106B (e.g., on the sides thereof).

Figure 1C:
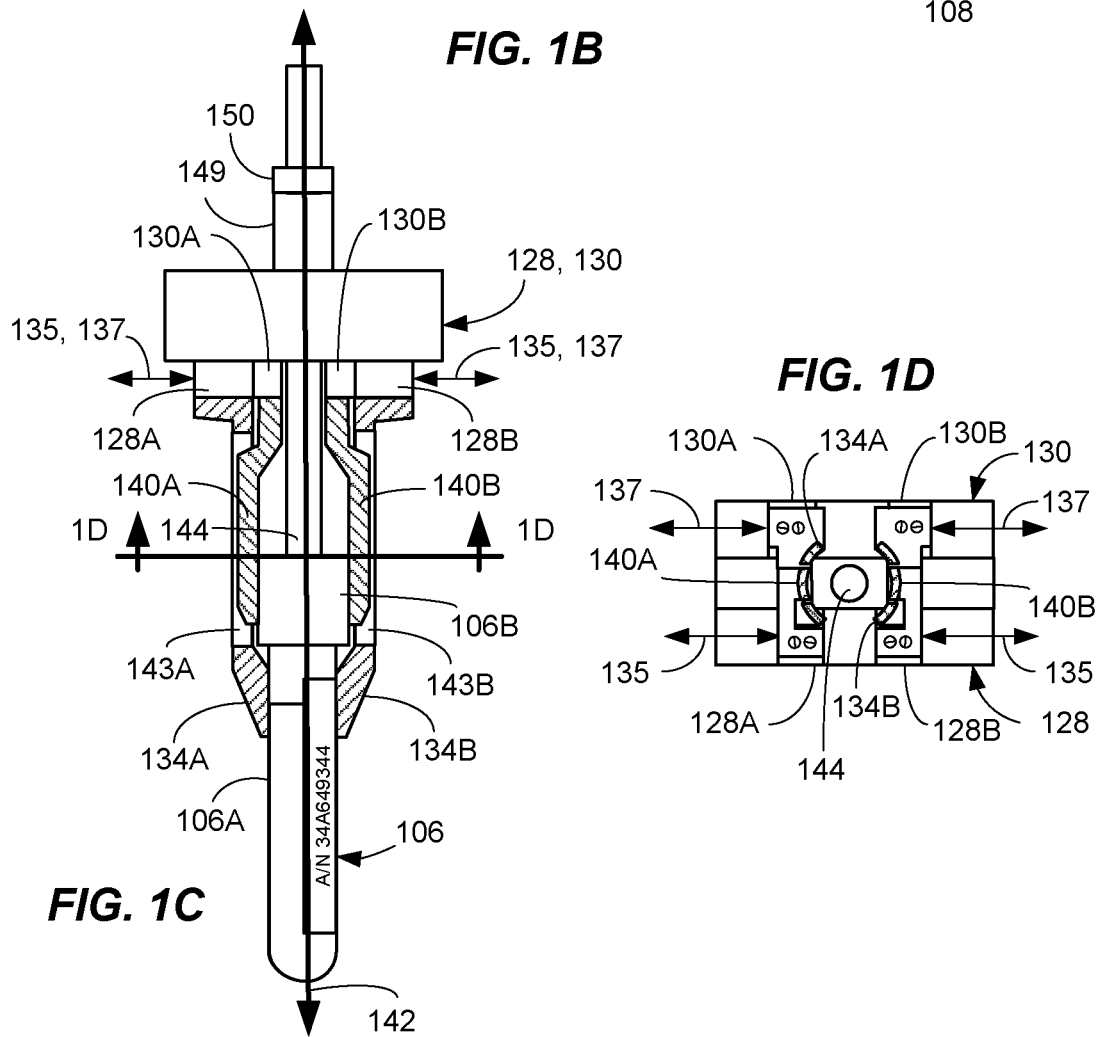
FIG. 1C is a partially cross-sectioned side view of an alternative gripper apparatus according to aspects of the present invention.
Figure 1D:
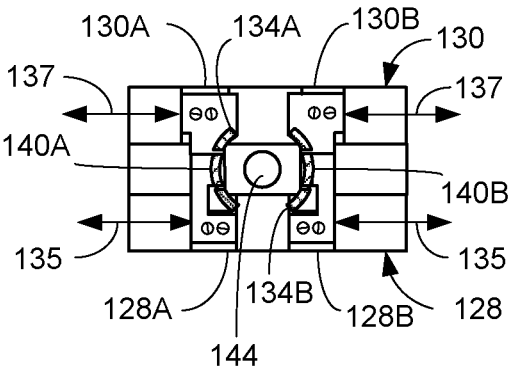
FIG. 1D is an underside view of a gripper apparatus of FIG. 1C taken along section line 1D-1D.

In some alternative embodiments, the fingers 134A, 134B and fingers 140A, 140B may be aligned along a gripper axis 142 and each pair may be positioned in an opposed orientation across the gripper axis 142. In some embodiments, one pair of fingers may be recessed within another pair thereby enabling the gripping action to be provided along a same transverse direction (e.g., horizontal) in a relatively confined space. This may be required when one of the locations from which the sample containers 106 are transferred to and from is a sample rack 108 including many tightly spaced sample containers 106 (see FIG. 1B). For example, as shown in the embodiment of FIG. 1C, a portion of fingers 140A, 140B may be received in recesses 143A, 143B formed in the fingers 134A, 134B. In some embodiments, the second pair 140A, 140B adapted to grip the cap 106B are shorter in length that the first pair 134A, 134B.

Figure 1E:
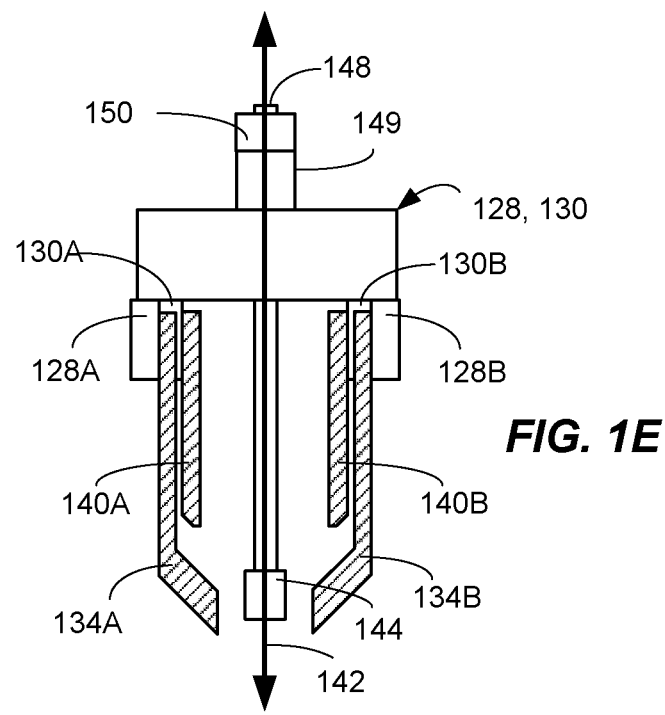
FIG. 1E is a partially cross-sectioned side view of an alternative gripper apparatus including a seating member shown fully extended according to aspects of the present invention.
Figure 1F:
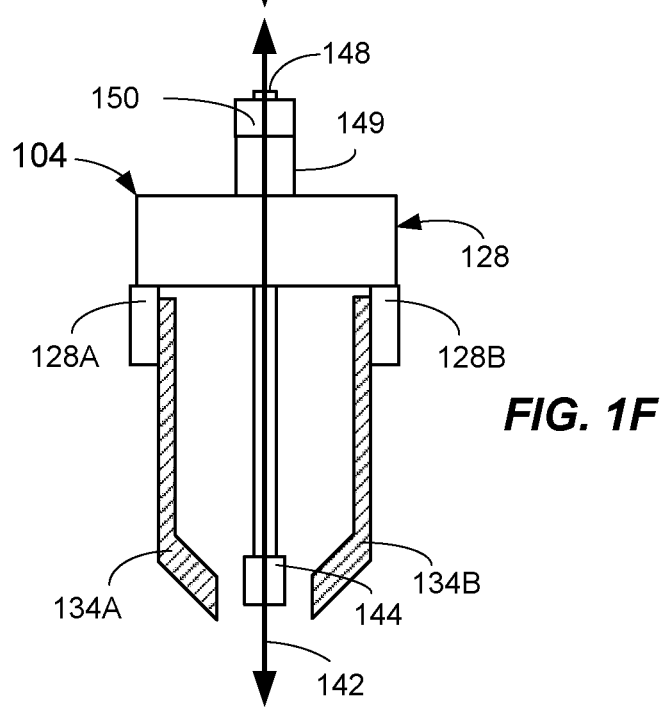
FIG. 1F is a partially cross-sectioned side view of an alternative gripper apparatus including a seating member shown fully extended according to aspects of the present invention.

According to another broad aspect as described in FIG. 1F, the gripper apparatus 104 may include only a single gripper component 128 including a first and second moveable jaws 128A, 128B wherein a first finger 134A is coupled to the first moveable jaw 128A, and a second finger 134B is coupled to the second moveable jaw 128B. In operation, the first and second fingers 134A, 134B are adapted to grip a sample container 106 (not shown) as in the aforementioned embodiments. Additionally, a seating member 144 may be provided and positioned adjacent to the first and second fingers 134A, 134B and may be moveable (e.g., translatable) along the gripper axis 142.

The seating member 144 may be any suitable member adapted and functioning to contact the cap 106B. For example, the seating member 144 may be a cylindrically-shaped puck. Optionally, the seating member 144 may simply be an end of a rod or shaft. The translation capability (extension and retraction) of the seating member 144 may be provided by a shaft 148 being constrained in movement to a direction parallel to (preferably coincident with) the gripper axis 142. The motion constraint may be provided by any suitable slide member, such as bearings (e.g., linear bearings) or bushings (not shown) engaging the shaft 148. Controlled linear motion of the seating member 144 along the gripper axis 142 may be provided by any suitable linear motion-producer 149, such as a linear motor, linear servo motor, linear drive, drive motor and gear assembly, etc. A sensor 150 (or a plurality of sensors) may be provided to sense a position of the seating member 144 along the gripper axis 142 and provide position information to a suitable position controller 146 for determining a position of the seating member 144. The sensor 150 may be an LVDT, for example. Other sensors adapted to sense linear motion may be utilized. If gripping only the tube body 106A of the sample container 106 is sought together with excellent position control, the gripper apparatus 104 of FIG. 1E consisting of a single jaw pair and a seating member 144 may be inserted in place of the gripper apparatus 104 of FIG. 1A.

A similar seating member 144, linear motion-producer 149, and sensor 150 as described above may also be provided in the embodiments of FIGS. 1A and 1E, and FIGS. 1C and 1D. Each linear motion-producer 149 driving each seating member 144 may be electrically coupled to a seating member position control 146 that may be adapted to drive the seating member 144 to any preprogrammed extension or retraction position alongside the first and second fingers 134A, 134B.

In operation, the seating member 144 may be adapted to contact a cap 106B of the sample container 106 at various times during the transfer cycle of the sample container 106. For example, when the first and second fingers 134A, 134B are in an opened configuration, and the gripper apparatus 102 has been arranged to pick a sample container 106 at a first location (e.g., from a sample rack 108), the seating member 144 may be fully or nearly fully extended. For example, as shown in FIG. 1E, the seating member 144 may be positioned towards the ends of the fingers 134A, 134B wherein the fingers 134A, 134B are shown in an opened configuration. As should be recognized, this aspect of the invention only requires a single pair of fingers operative with the seating member 144. However, additional fingers (e.g., fingers 140A, 140B) may be employed when it is desired to grip both the sample tube body 106A and the cap 106B.

The control of the motion of the fingers 134A, 134B and fingers 140A, 140B may be accomplished by first finger pair control 151 and by second finger pair control 153 that are coupled with the gripper components 128, 130, respectively. The coupling may be electrical when the gripper components 128, 130 are electrical. The coupling may be to a servo, pumping mechanism, or valve when the gripper components 128, 130, are hydraulic or pneumatic. The respective opening and closing of fingers 134A, 134B and 14A, 140B may be appropriately controlled via suitable control signals from finger pair controls 151, 153 according to a preprogrammed routine. The motion of the fingers 134A, 134B and 14A, 140B is preferably coordinated with the operation of the seating member 144.

Additionally, the sample container transfer system 100 may include a limiting device 155. The limiting device 155 may be a linear clutch, a crash slide, or other force or motion limiting device. The limiting device 155 may be mounted on or to the gripper apparatus 104 or elsewhere between the robot apparatus 102 and the gripper apparatus 104. For example, the limiting device 155 may be mounted to a bracket 156 which attaches to the gripper apparatus 104. The limiting device 155 may receive a vertical shaft 158 of the robot apparatus 102. The limiting device 155 may function to detect collisions (via exceeding a preset load) and break away (e.g., along the Z-axis) by allowing shaft 158 to slide in the limiting device 155. This enables the gripper apparatus 104 to stop its motion progression in the Z-axis direction and thereby prevent overloading of the fingers 134A, 134B and/or 140A, 140B, the sample container 106, or any other component in the load path of the sample container transfer system 100, as well as the pick or place destinations.

Figure 2A:
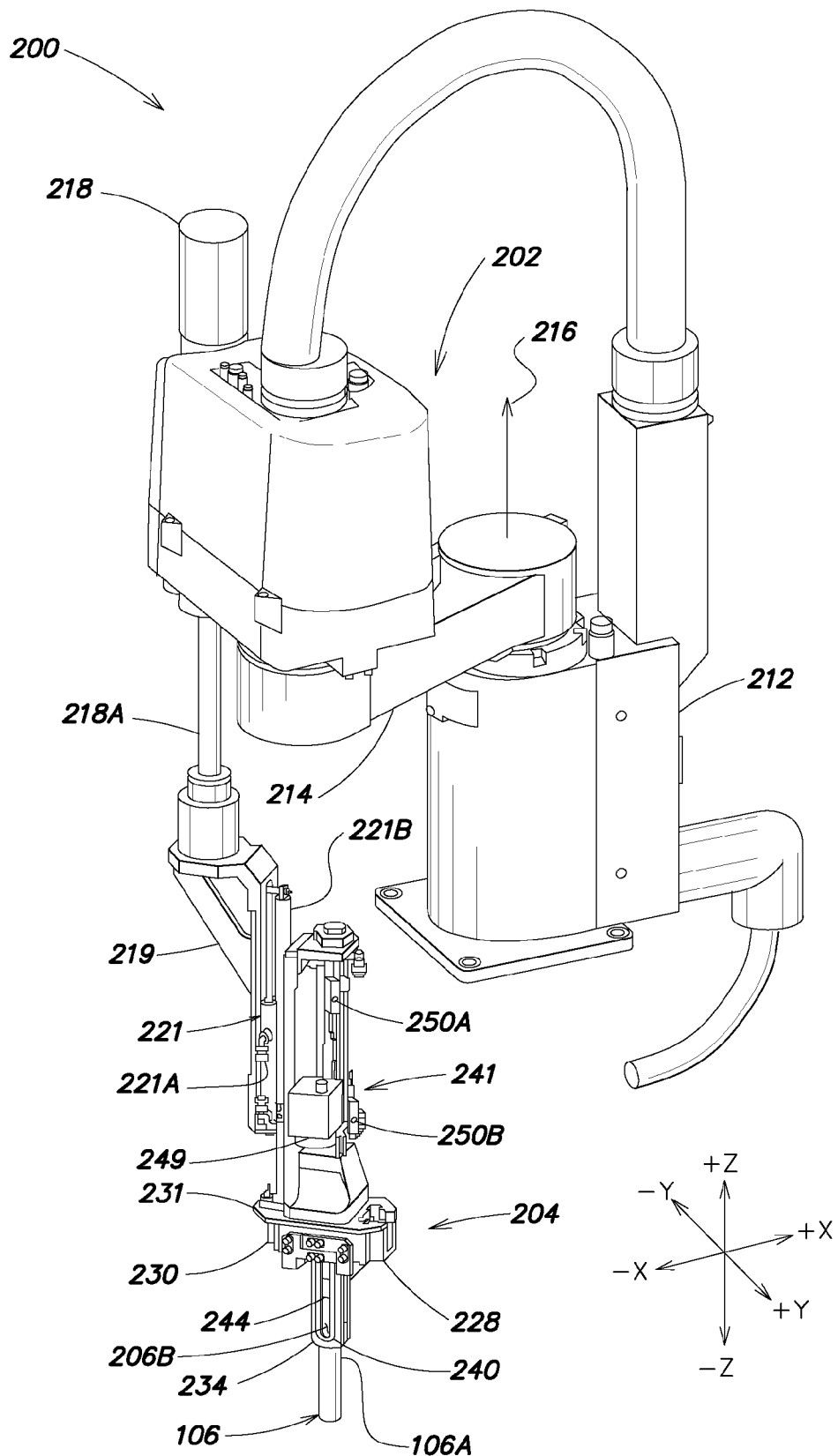
FIG. 2A is a perspective view of an exemplary embodiment of a sample container transfer system according to aspects of the present invention.
Figure 2B:
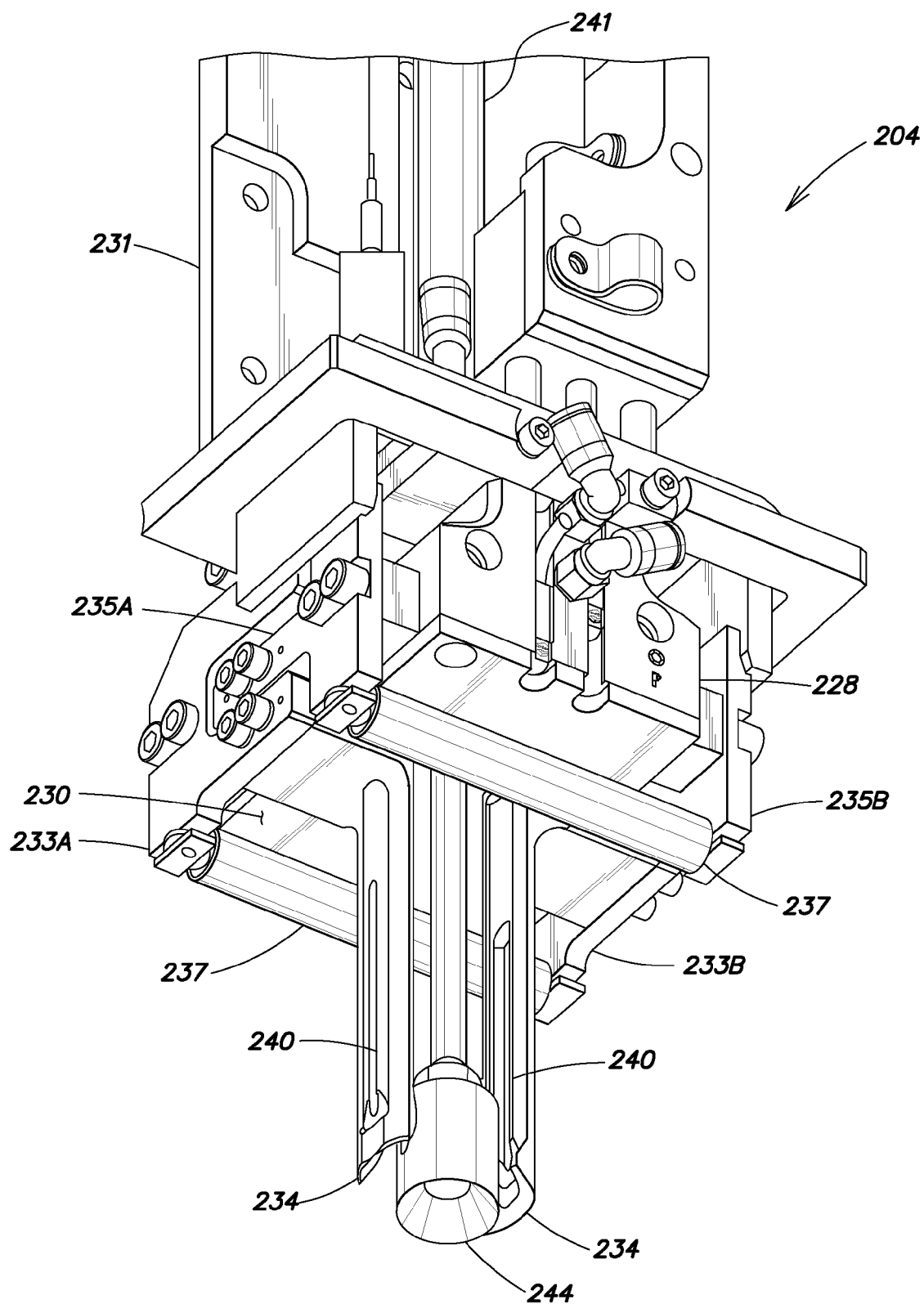
FIGS. 2B-2C are perspective views of an exemplary embodiment of a gripper apparatus according to aspects of the present invention.
Figure 2C:
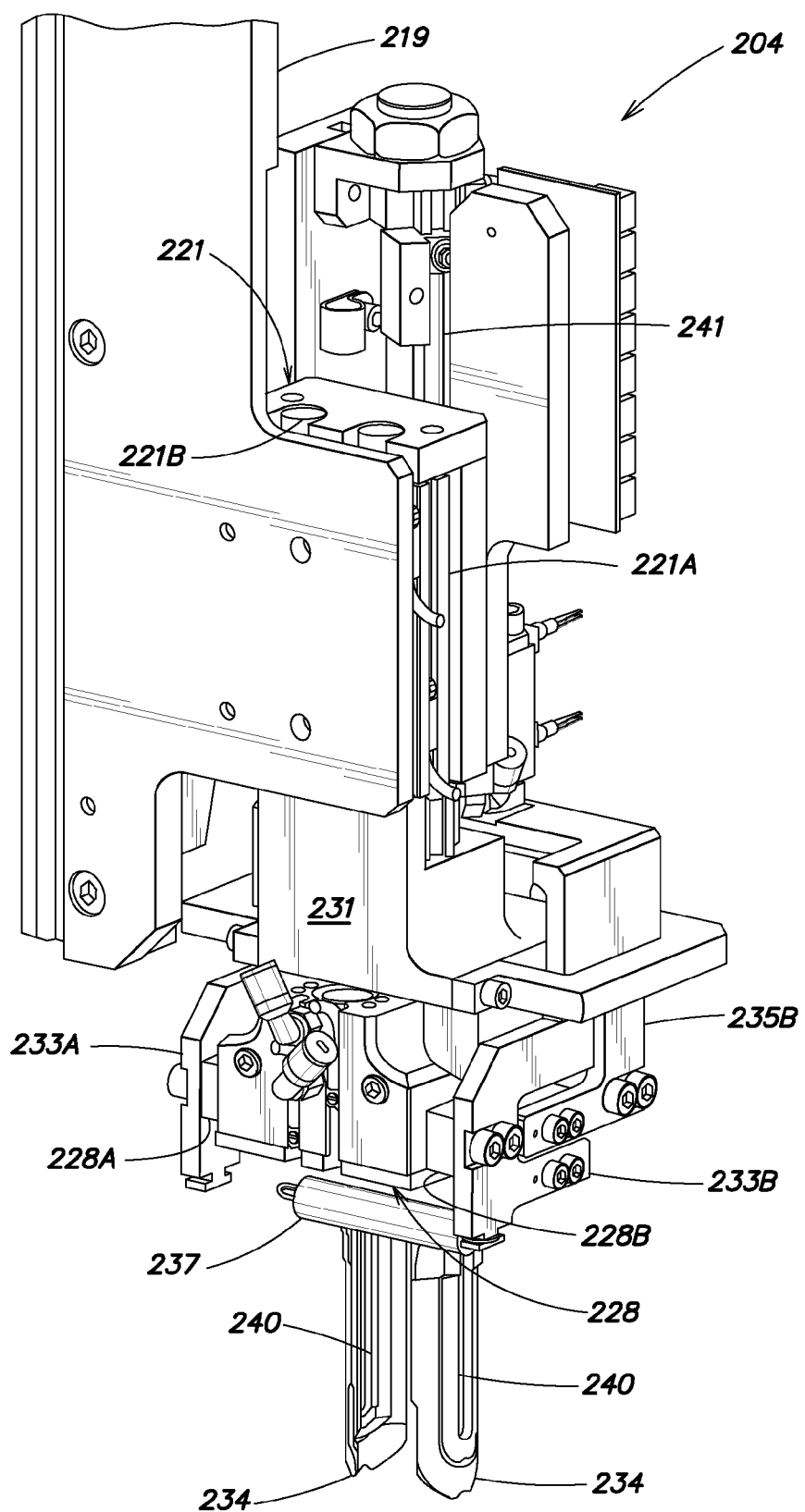

Another embodiment of a sample container transfer system 200 including a gripper apparatus 204 is shown in FIGS. 2A-2C. As in the previously-described embodiments, the sample container transfer system 200 includes a robot apparatus 202 and a gripper apparatus 204. The robot apparatus 202 includes a rotational motor 212 adapted to cause rotation of an arm assembly 214 which causes rotation of the gripper apparatus 204 about axis 216. Vertical motion of the gripper apparatus 204 may be provided by vertical motor 218 which cases shaft 218A to move vertically up (+Z) and down (−Z). The shaft 218A may be coupled to a bracket assembly 219, which in turn may be coupled to the gripper apparatus 204.

The bracket assembly 219 may include a limiting device 221 such as a linear clutch apparatus that functions to limit a load that may be applied to the gripper apparatus 204 in the vertical direction (+Z) along the Z axis. The limiting device 221 may include a clutch portion 221A which slips upon encountering a designed pre-established force level. The clutch portion 221A may frictionally engage a clutch shaft or shafts (see FIG. 2C) 221B and relative motion between the clutch portion 221A and the clutch shaft(s) 221B may occur when the predefined load is exceeded. Anti-rotation of the clutch shaft 221B relative to the clutch portion 221A may be provided, such as by a key and keyway, use of more than one shaft, or other suitable mechanism. Once the load is removed, the gripper apparatus 204 may substantially freely return to a neutral position (e.g., an un-tripped position).

As in the previous embodiments, dual moveable-jaw gripper components 228, 230 are provided. These components 228, 230 may be mounted on and coupled to a bracket 231. Movement of the gripper components 228, 230 causes motion (opening and closing) of the finger pairs 234, 240. In particular, connector brackets 233A, 233B and 235A, 235B connect between the jaws 228A, 228B, 230A, 230B of the gripper components 228, 230 and the finger pairs 234, 240. One or more springs 237 may connect between the respective brackets (e.g., 233A, 233B and 235A, 235B) to ensure safe failure of the gripper component 228 to a closed condition. The spring 237 is shown unconnected in FIG. 2C. The lower finger pair 234 is adapted to grip the tube body 106A of the sample container 106, whereas the upper pair 240 is adapted to grip the cap 106B.

A seating assembly 241 may also be coupled and mounted to the bracket 231. The seating assembly 241 functions to cause the vertical motion of the seating member 244. The seating assembly 241 may include a vertical motor 249 adapted to cause the motion of the seating member 244, the seating member 244, and sensors. Various sensors 250A, 250B may be provided for providing feedback information about a location of the seating member 244. For example, end switches may be used. Other types of position sensors may be used.

Referring now to FIGS. 3A-3G, various views of another embodiment of a gripper apparatus 304 are provided. As many of the elements are similar to the previously-described embodiments, the description is brief. The gripper apparatus 304 may include first and second gripper components 328, 330 each having moveable jaws 328A, 328B, 330A, 330B, first and second fingers 334A, 334B coupled to the moveable jaws 328A, 328B via plate-like connector brackets 333A, 333B; second and third fingers 340A, 340B coupled to the moveable jaws 330A, 330B via the plate-like connector brackets 335A, 335B; seating member 344, shaft 348, linear motion-producer 349, limiting device 355, and bracket 356. As can be clearly seen, one or more of the fingers 340A, 340B may include serrations along their gripping surfaces to aid in gripping the cap 106B. In this embodiment, the seating member 344 is provided as an end of a rod that connects to the shaft 348.

Figure 3A:
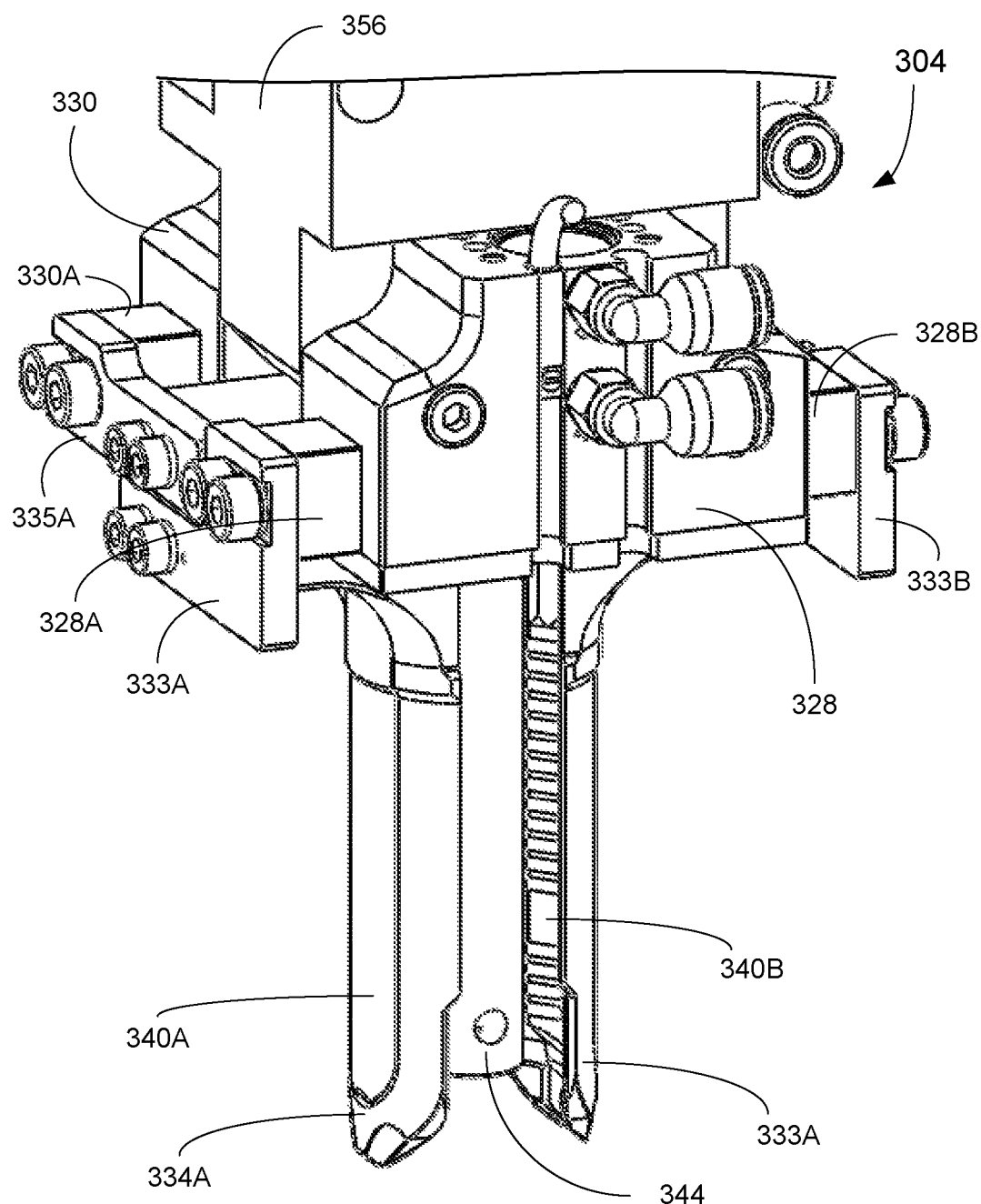
FIG. 3A is a perspective view of another exemplary embodiment of a gripper apparatus according to aspects of the present invention.
Figure 3B:
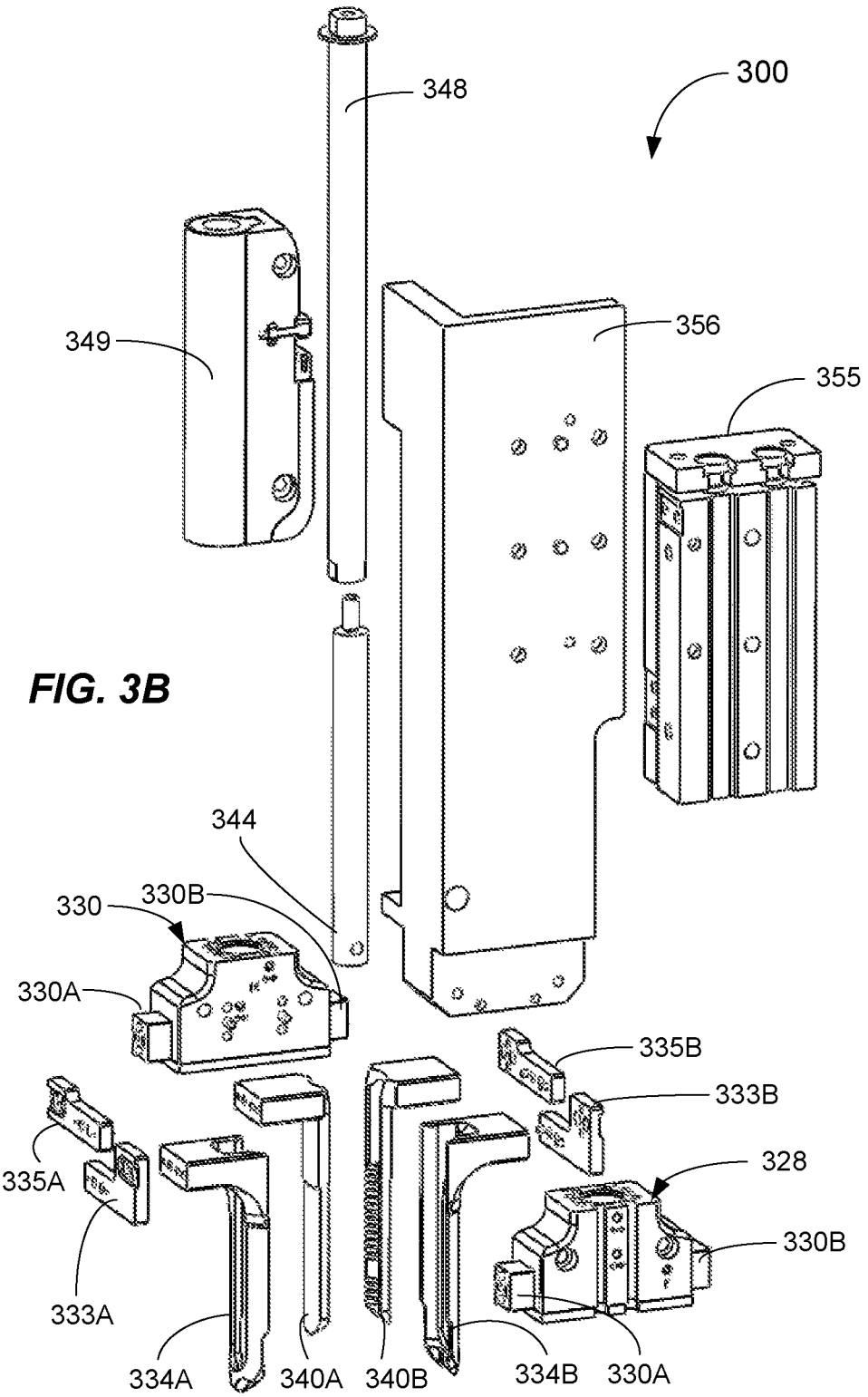
FIG. 3B is an exploded view illustrating various components of the exemplary embodiment of a gripper apparatus of FIG. 3A.
Figure 3C:
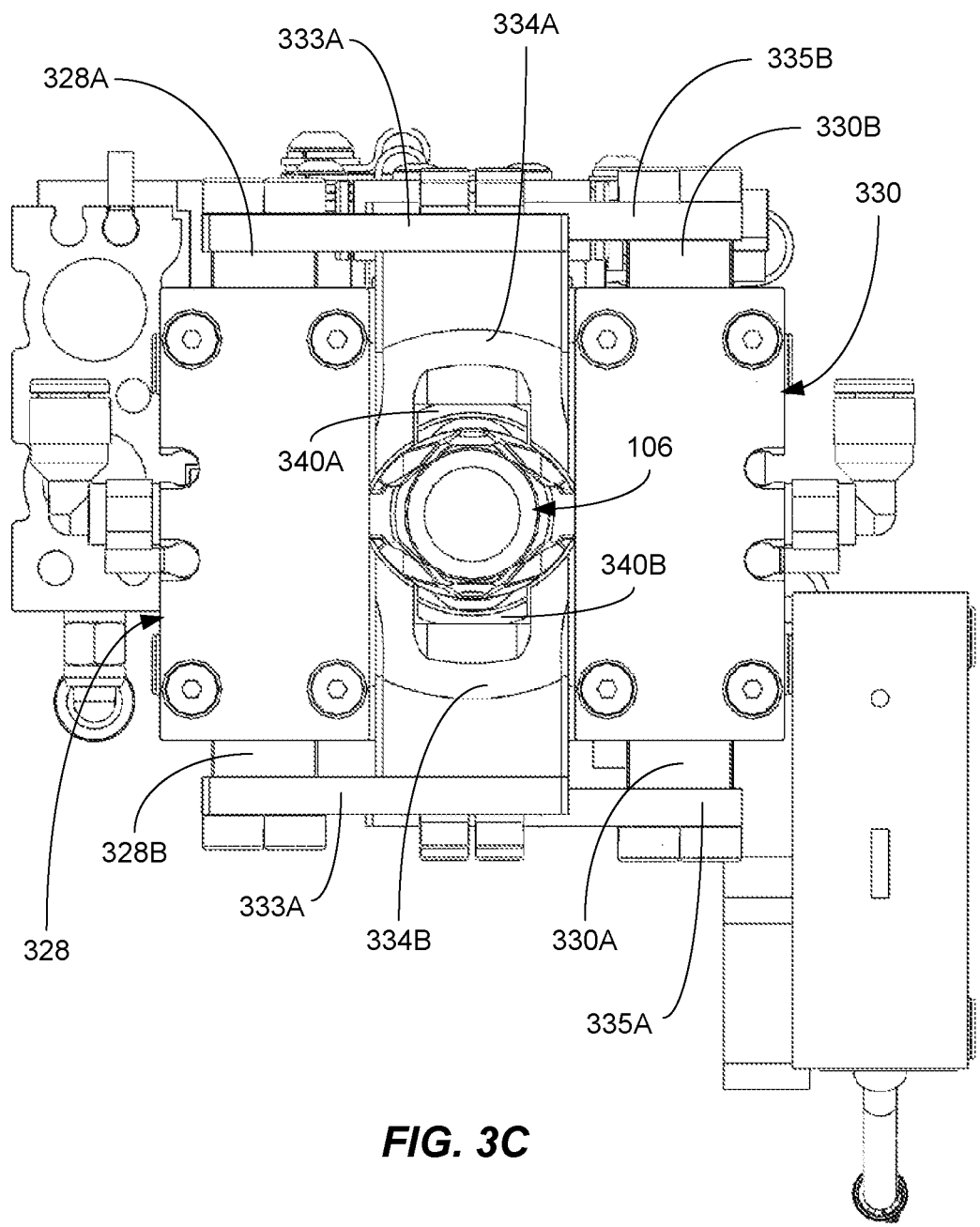
FIG. 3C is an underside view the embodiment of a gripper apparatus of FIG. 3A.
Figure 3D:
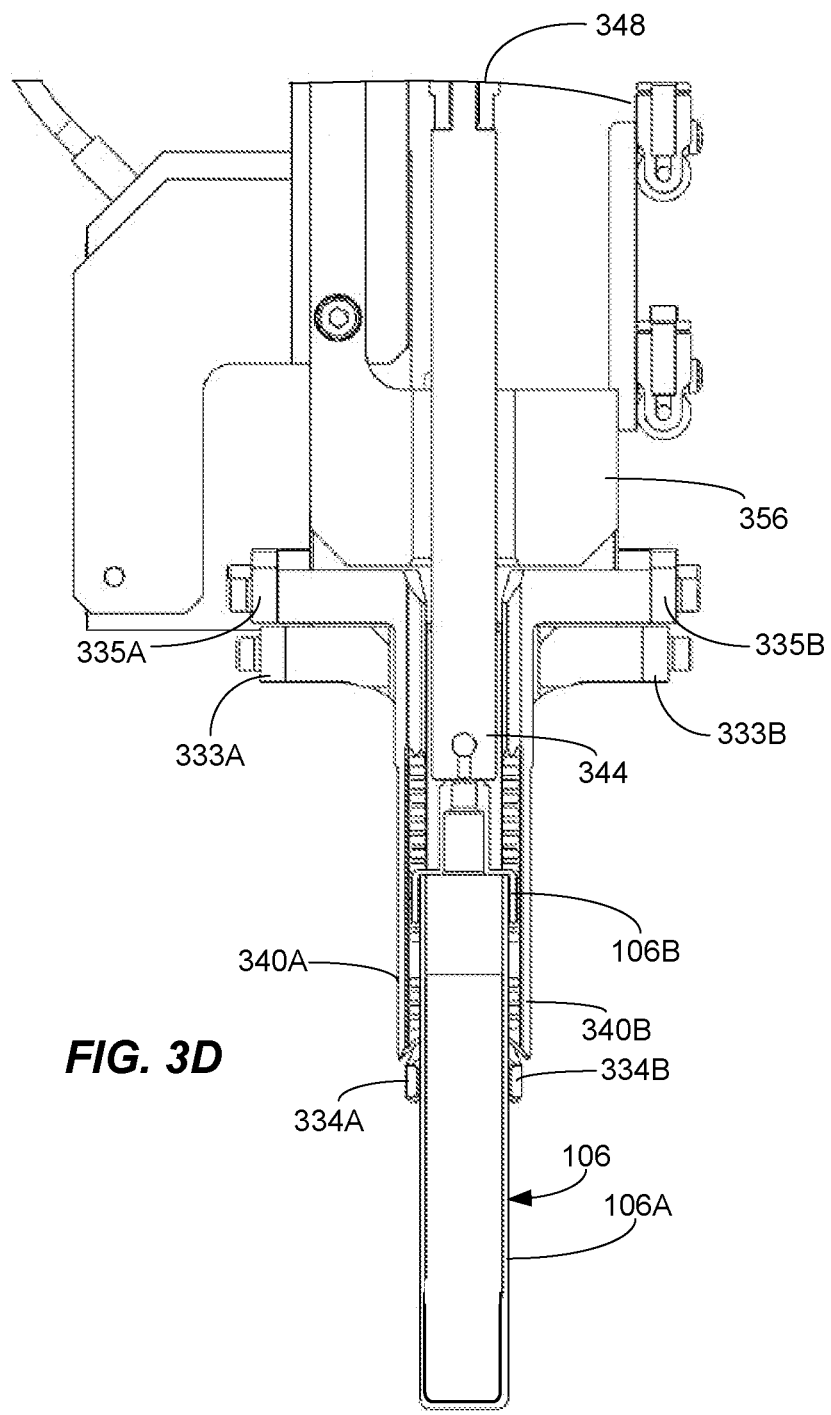
FIG. 3D is a partial, cross-sectioned side view of the embodiment of a gripper apparatus of FIG. 3A gripping a sample container.
Figure 3E:
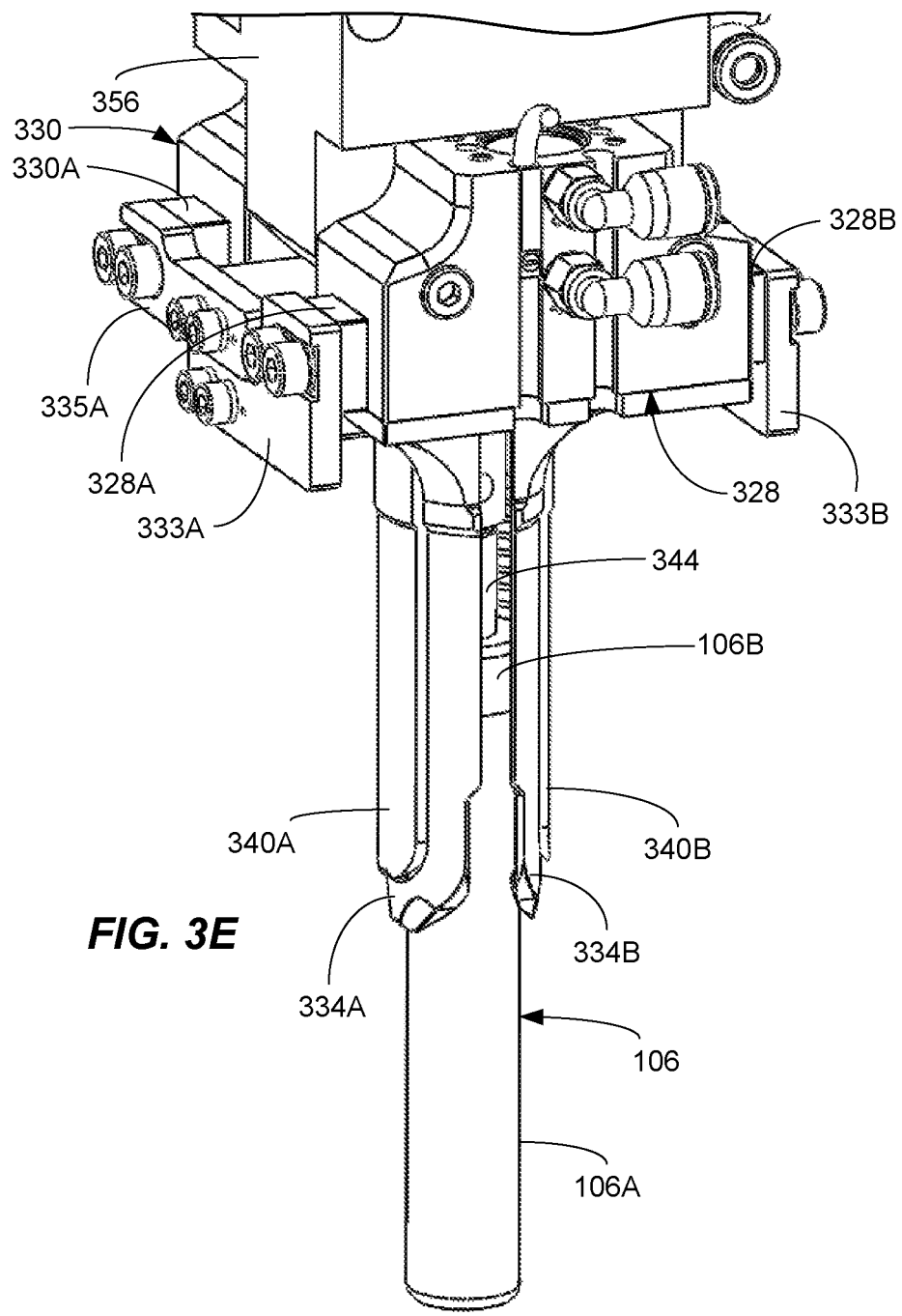
FIG. 3E is a perspective view the embodiment of a gripper apparatus of FIG. 3A shown gripping a sample container.
Figure 3F:
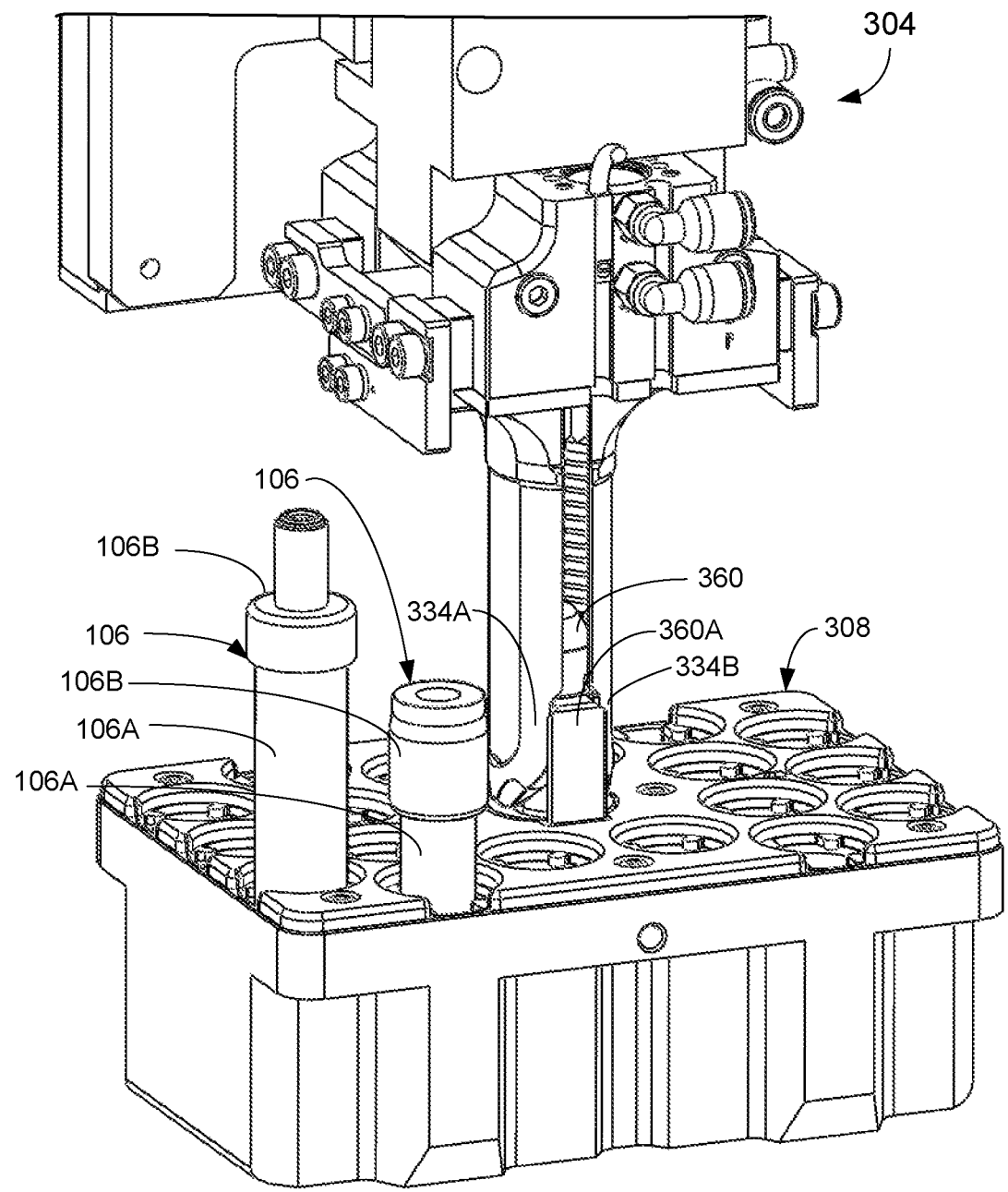
FIG. 3F is a perspective view the embodiment of a gripper apparatus of FIG. 3A shown gripping a post of an exemplary sample rack.

FIG. 3F illustrates the gripper apparatus 304 located at a first location. Several sample containers 106 are received in the sample rack 308 and are illustrated having different heights of the sample tube body 106A and different configurations of caps 106B. The present invention is adept at picking such sample containers 106 having different shapes and configurations from a sample rack 308 and then placing these picked sample containers 106 at a second location. In addition, the pick operation may actually transfer the sample rack from a first location to a second location. FIG. 3F illustrates performing a sample rack pick operation at a first location. On this sample rack, a central post 360 that mimics a tube and cap configuration extends from a body of the sample rack 308. The central post 360 includes one or more side extenders 360A that extend laterally from the post body and are adapted to register on one or more sides of the finger pair 334A, 334B. Notches may be formed on one or more sides of the fingers 334A, 334B, and the notches having an approximate shape of the portion of the side extender 360A that it is engaged with to further aid with registration. The side extenders 360A help keep the sample rack 308 rotationally aligned so that the place operation of the sample rack 308 may be precisely carried out with the orientation of the sample rack 308 relative to the gripper apparatus 304 being known.

Figure 3G:
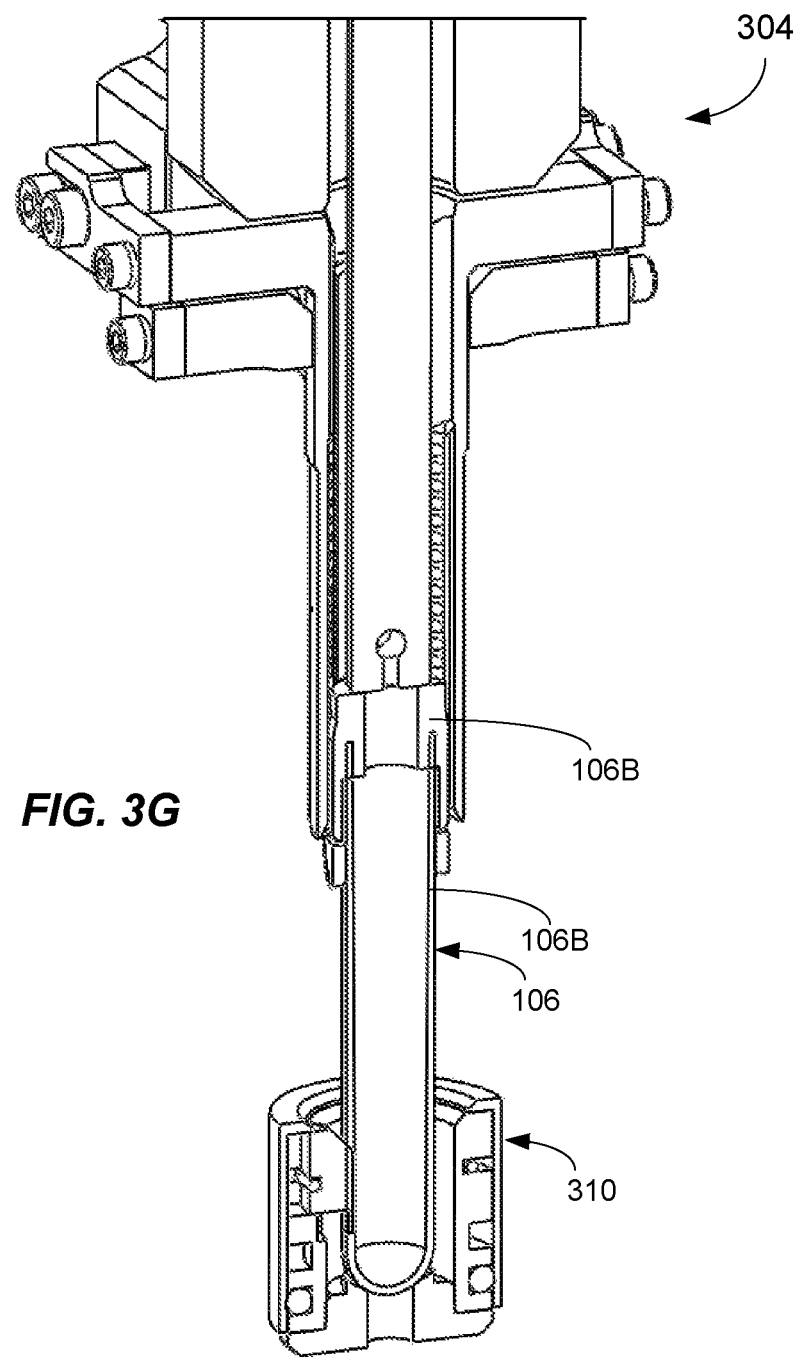
FIG. 3G is a partial, cross-sectioned perspective view the embodiment of a gripper apparatus of FIG. 3A gripping a sample container inserted into a receptacle.

FIG. 3G illustrates an operation by the gripper apparatus and robot apparatus (not shown in FIG. 3G) where the sample container 106 including sample tube body 106A and cap 106B are inserted into a receptacle 110 (shown cross sectioned) as part of a place operation. The receptacle 310 may receive the sample container 106 and be used to carry the container to various pre-processing operations or to a clinical analyzer for testing.

Figure 4A:
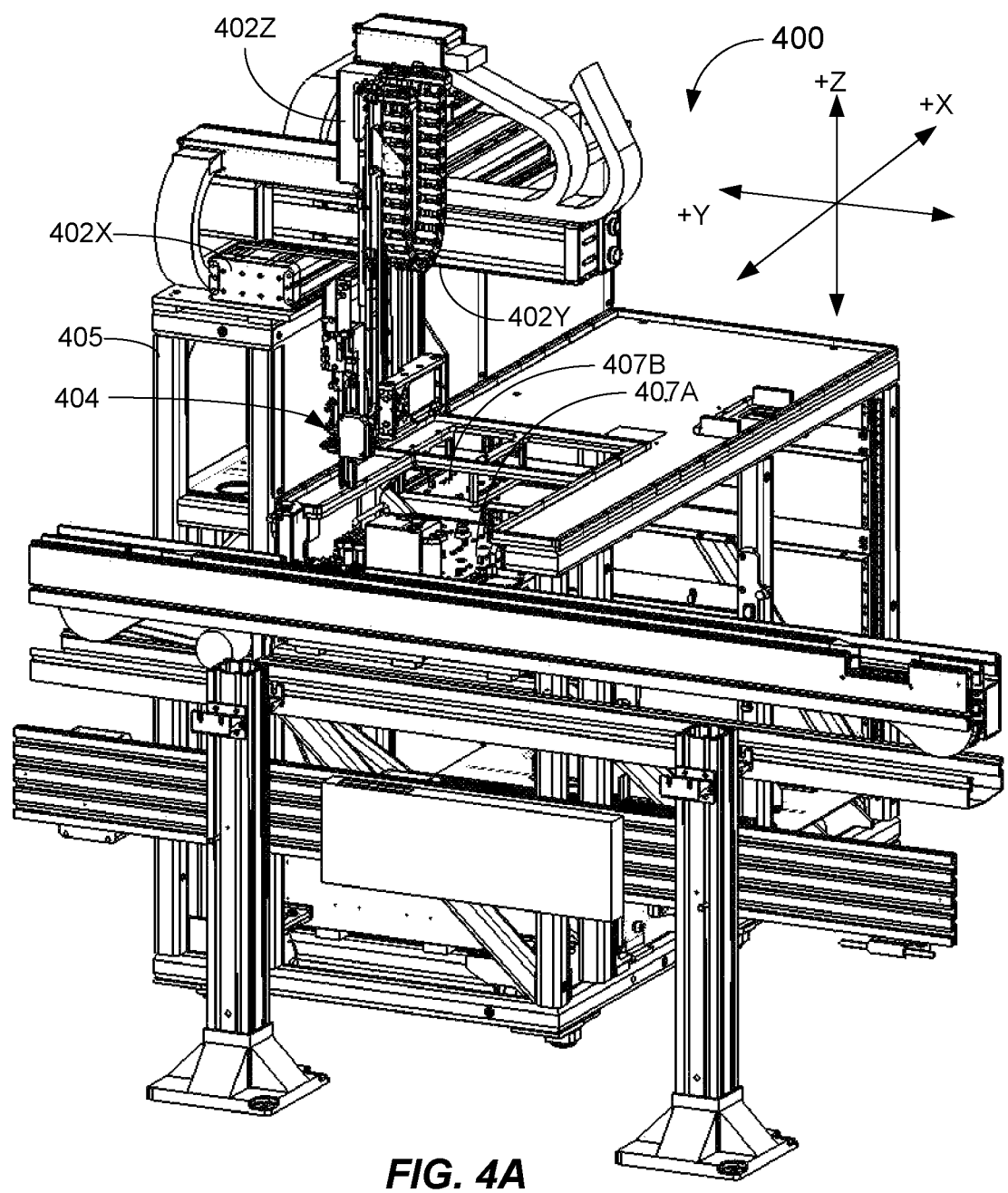
FIG. 4A is a perspective view of another exemplary embodiment of a sample container transfer system according to aspects of the present invention.
Figure 4B:
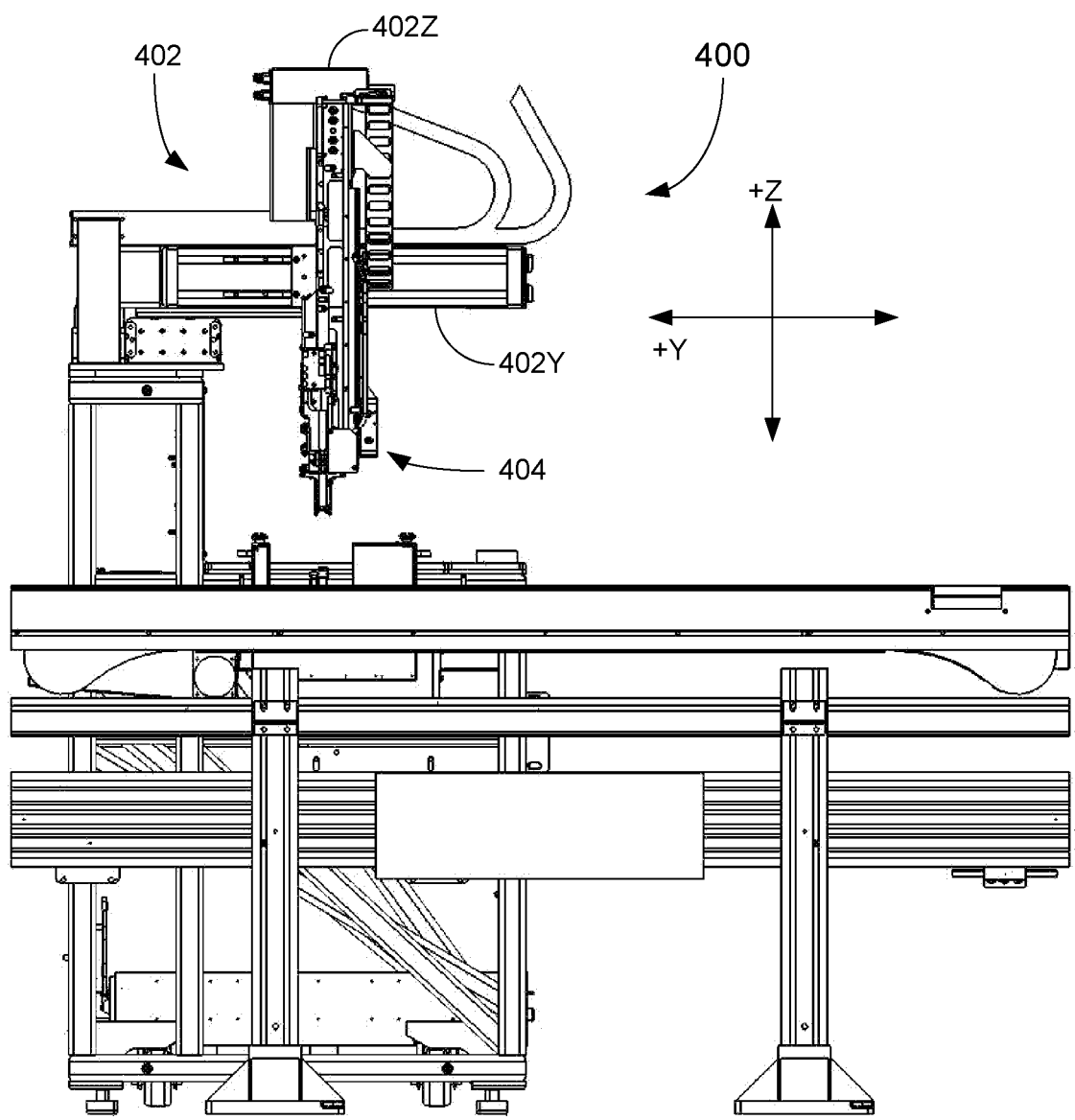
FIG. 4B is a side view of the exemplary embodiment of sample container transfer system of FIG. 4A.
Figure 4C:
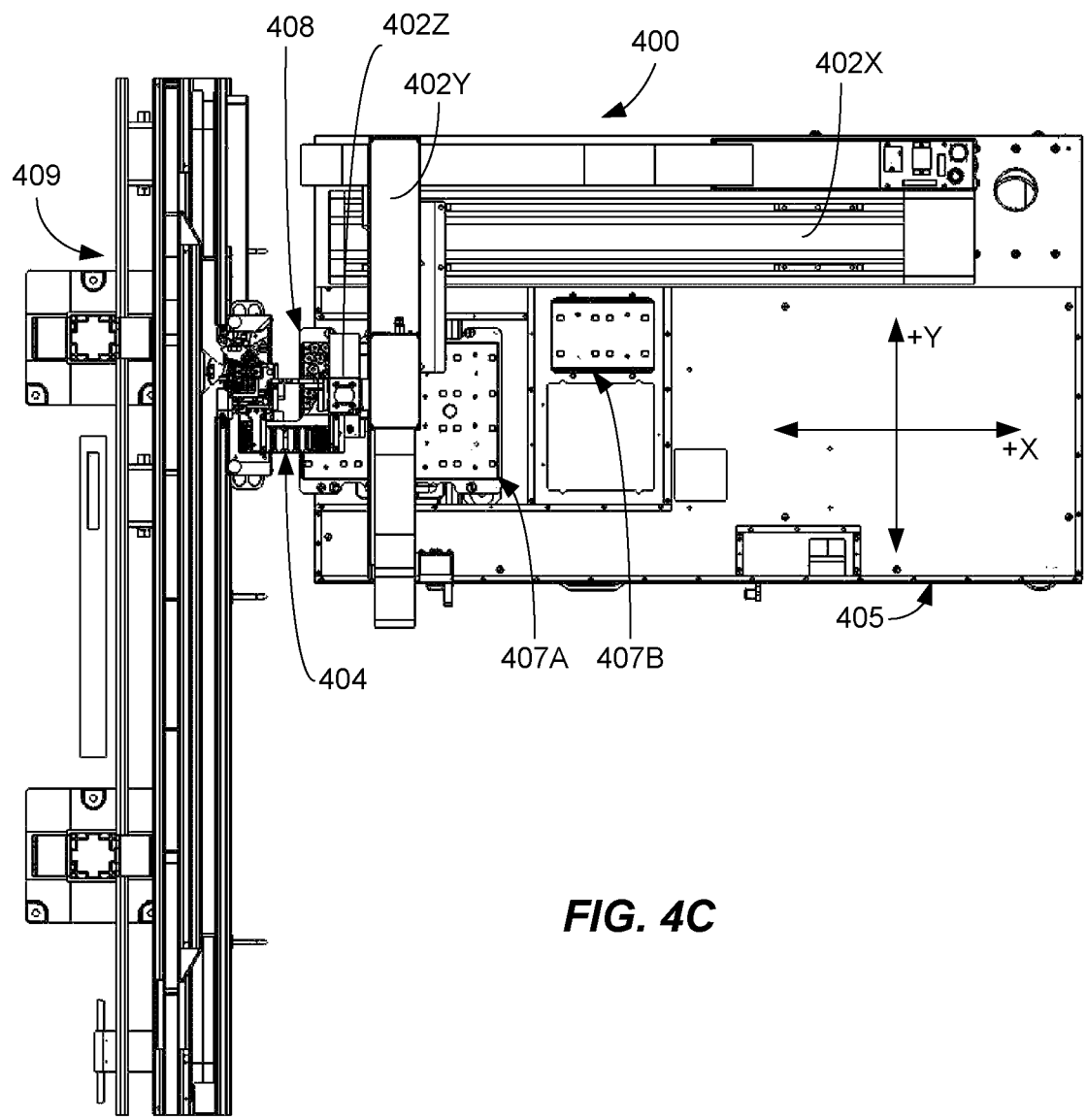
FIG. 4C is a top view of the exemplary embodiment of sample container transfer system of FIG. 4A.

Referring now to FIGS. 4A-4C, various views of another embodiment of a sample container transfer system 400 are provided. In this embodiment, the robot apparatus 402 is a multistage robot apparatus including a linear x-axis stage 402X, a linear Y-axis stage 402Y, and a linear Z axis stage 402Z for carrying out X-axis, Y-axis, and Z-axis motions of the gripper apparatus 404 thereby allowing the three-axis motion of a sample container (e.g., 106) gripped by the gripper apparatus 404. The gripper apparatus 404 may be any of the aforementioned gripper apparatus types as shown and described with reference to FIGS. 1A-1E, FIGS. 2A-2C, and FIGS. 3A-3G, for example.

The robot apparatus 404 may be mounted on any suitable frame 405. The frame 405 may include one or more trays 407A, 407B mounted thereon at various fixed locations. The trays may receive one or more sample racks 408 in fixed locations thereof. For example, the locations of the sample racks 408 may be fixed by pins projecting from the trays 407A, 407B and the pins may be received in bores or slots (not shown) formed in the bottom of the sample racks 408. Multiple sample containers (e.g., 10^) may be may be registered in the sample racks 408. Sample racks 408 may be the same as is shown in FIG. 3F, for example.

A suitable position controller (not shown) may cause the robot apparatus 402 to move the gripper apparatus 404 in one or more of the X, Y and Z directions and preferably in all three. The gripper apparatus 404 may pick a sample container (e.g., 106) from a rack 408 and transfer the sample container to a clinical analyzer or other pre-processing equipment. In the depicted embodiment, the sample container (e.g., 106) is inserted into a receptacle of a centrifuge apparatus 409 that may carry out a preliminary step of centrifugation of one or more specimens contained in one or more sample containers. However, it should be recognized that the current sample container transfer apparatus 400 may be used to feed sample containers (e.g., 106) to and from any type of analyzer or piece of equipment that processes sample containers and for which a high level of automation is sought. After completion of processing of all of the sample containers within the sample rack 408, the rack 408 itself, and the included sample containers may be placed on a conveyor destined for a next processing operation, such as another clinical analyzer or another pre-processing station.

Figure 5:
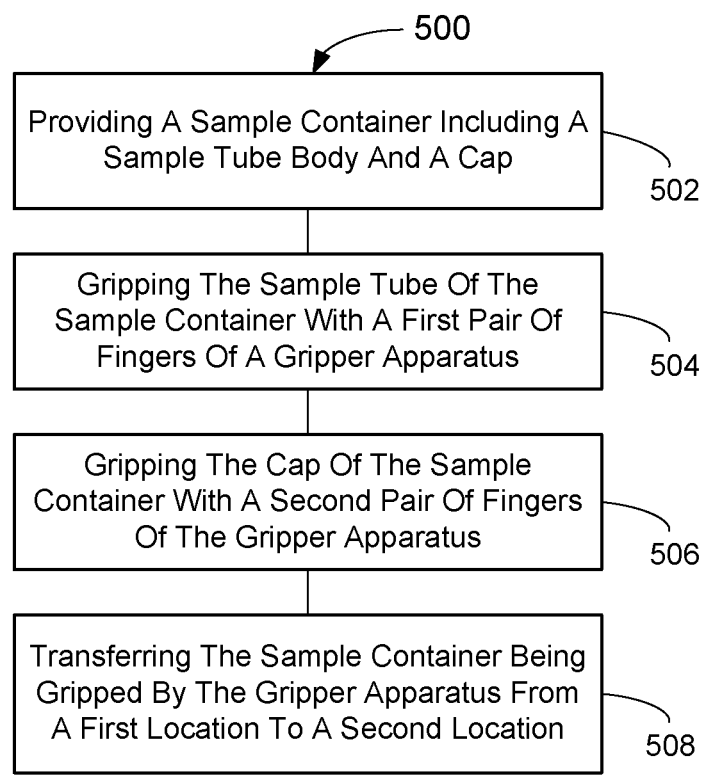
FIG. 5 is a flowchart illustrating methods according to embodiments of the present invention.

Referring now to FIG. 5, a broad method of transferring a sample container according to a first aspect of the invention is illustrated. The method 500 includes the steps of providing a sample container 106 including a sample tube body 106A and a cap 106B in 502. In 504, the sample container 106 is gripped by the sample tube 106A by a first pair of fingers (e.g., fingers 134A, 134B). In 506, the sample container 106 is gripped by the cap 106B by a second pair of fingers (e.g., fingers 140A, 140B). In this way, excellent gripping and position control of the sample container 106 may be accomplished. Following the gripping of the sample tube body 106A and cap 106B, the sample container 106 may be transferred from a first location to a second location by the gripper apparatus (e.g., 104) via control of the robot apparatus (e.g., 102) by robot position control subsystem 122. For example, the sample container 106 may be transferred from a sample rack 108 (see FIG. 1B) to a receptacle 110 (see FIG. 1A) and then inserted in the receptacle 110.

Figure 6:
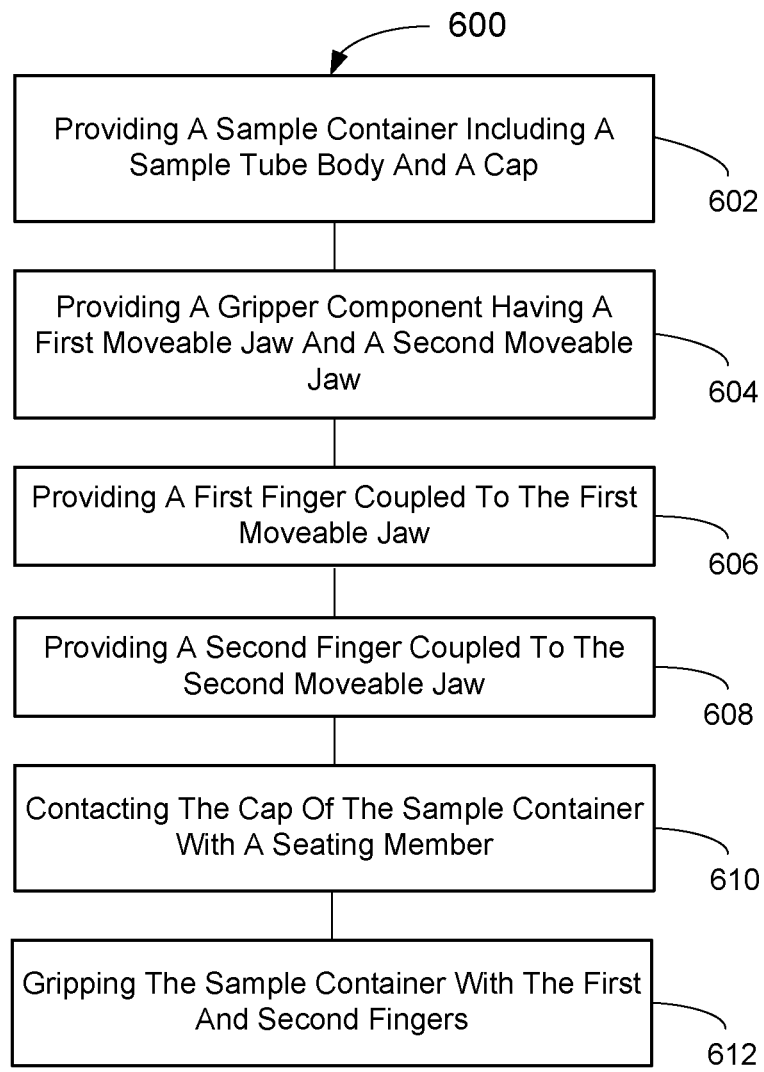
FIG. 6 is a flowchart illustrating other methods according to embodiments of the present invention.

Referring now to FIG. 6, a broad method of transferring a sample container 106 according to another aspect of the invention is illustrated. The method 600 may include the steps of providing a sample container 106 including a sample tube body 106A and a cap 106B in 502. In 604, a gripper component (e.g., 128) is provided that includes a first moveable jaw (e.g., 128A) and a second moveable jaw (e.g., 128B) each arranged alongside of a gripper axis (e.g., 142). In 606, a first finger (e.g., 134A) is provided that is coupled to the first moveable jaw, and in 608 a second finger (e.g., 134B) is provided that is coupled to the second moveable jaw. In 610, the cap 106B of the sample container 106 is contacted with a seating member (e.g., 144). The seating member may be moveable along the gripper axis (e.g., 142), and may be positioned adjacent to the first and second fingers. Preferably, the cap 106B is contacted when the first and second fingers are in an opened configuration. Once the position of the sample container is determined via contacting the cap, the sample container may be gripped with the first finger and the second finger in 612.

In some embodiments, the sample container 106 is gripped by the sample tube 106A by the first pair of fingers (e.g., fingers 134A, 134B), and simultaneously gripped by the cap 106B by a second pair of fingers (e.g., fingers 140A, 140B). Following the gripping, the sample container 106 may be transferred from a first location to a second location by the gripper apparatus (e.g., 104) via control of the robot apparatus (e.g., 102). For example, the robot apparatus (e.g., 102) and gripper apparatus (e.g., 104) may perform a place operation wherein the sample container 106 is first inserted into a receptacle (e.g., 110) to a first depth position within the receptacle, and then the seating member (e.g., 144) contacts the cap 106B of the sample container 106 to move the sample container 106 to a second deeper position within the receptacle 110. In another embodiment of the method, the robot apparatus (e.g., 102) and gripper apparatus (e.g., 104) may perform a pick operation wherein the cap 106B of the sample container 106 is first contacted with the seating member (e.g., 144) in an extended configuration prior to gripping of both of the sample tube body 106A and the cap 106B of the sample container 106 by the first finger pair (e.g. 134A, 134B) and the separate second finger pair (e.g., 140A, 140B).

It should be readily appreciated by those persons skilled in the art that the present invention is susceptible of broad utility and application. Many embodiments and adaptations of the present invention other than those herein described, as well as many variations, modifications, and equivalent arrangements, will be apparent from, or reasonably suggested by, the present invention and the foregoing description thereof, without departing from the substance or scope of the present invention. Accordingly, while the present invention has been described herein in detail in relation to specific embodiments, it is to be understood that this disclosure is only illustrative and exemplary of the present invention and is made merely for purposes of providing a full and enabling disclosure of the invention. This disclosure is not intended to limit the invention to the particular systems, apparatus, or methods disclosed, but, to the contrary, the intention is to cover all modifications, equivalents, and alternatives falling within the spirit and scope of the invention.

What is claimed is:

1. A gripper apparatus, comprising:
    a gripper component including first and second moveable jaws arranged alongside of a gripper axis;
    a first pair of fingers including:
        a first finger coupled to the first moveable jaw; and
        a second finger coupled to the second moveable jaw, the first and second fingers are adapted to grip a sample container, the sample container including a tube body and a cap;
    a seating member positioned adjacent to the first and second fingers and moveable along the gripper axis, the seating member adapted to contact the cap of the sample container when the first and second fingers are in an opened configuration; and
    a linear motion-producer coupled to the seating member and configured to provide controlled linear motion to drive the seating member along the gripper axis; and
    a seating member position controller electrically coupled to the linear motion producer and adapted to drive the seating member to any preprogrammed extension or retraction position alongside the first and second fingers.

2. The gripper apparatus of claim 1 wherein the linear motion-producer is further configured to cause the seating member to push on the cap of the sample container to strip the sample container from the first and second fingers.

3. The gripper apparatus of claim 1 wherein the linear motion-producer is further configured to cause the seating member to move the sample container from a first position to a second position within a receptacle during a place operation when the first and second fingers are in an opened configuration.

4. The gripper apparatus of claim 1 wherein the first and second fingers are positioned in an opposed orientation across the gripper axis, the first and second fingers are coupled to a first gripper component including first and second moveable jaws configured to be actuated to open and close the first and second fingers.

5. The gripper apparatus of claim 4, further comprising a second pair of fingers including a third finger and a fourth finger, the third and fourth fingers being positioned in an opposed orientation across the gripper axis and adapted to grip the sample container, the third and fourth fingers are coupled to a second gripper component including third and fourth moveable jaws configured to be actuated to open and close the third and fourth fingers.

6. The gripper apparatus of claim 5 wherein the second pair of fingers are shorter in length than the first pair of fingers and the second pair of fingers is adapted to grip the cap.

7. The gripper apparatus of claim 1 further comprising a second pair of fingers including a third finger and a fourth finger, the third and fourth fingers being positioned in an opposed orientation across the gripper axis and adapted to grip the cap of the sample container and wherein the first pair of fingers is adapted to grip the tube body of the sample container.

8. The gripper apparatus of claim 7 wherein a portion of the third finger is received in a recess formed in the first finger and wherein a portion of the fourth finger is received in a recess formed in the second finger.

9. A sample container transfer system, comprising:
    a robot apparatus moveable in at least one coordinate direction; and
    a gripper apparatus coupled to, and moveable by, the robot apparatus, the gripper apparatus including
        a gripper component including a first moveable jaw and second moveable jaw each arranged alongside of a gripper axis,
        a first pair of fingers including:
            a first finger coupled to the first moveable jaw; and
            a second finger coupled to the second moveable jaw, the first and second fingers are each adapted to grip a sample container, the sample container including a tube body and a cap;
        a seating member positioned adjacent to the first finger and the second finger and moveable along the gripper axis, the seating member adapted to contact the cap of the sample container when the first and second fingers are in an opened configuration; and
        a linear motion-producer coupled to the seating member and configured to provide controlled linear motion to drive the seating member along the gripper axis;
        a seating member position controller electrically coupled to the linear motion producer and adapted to drive the seating member to any preprogrammed extension or retraction position alongside the first and second fingers to do at least one of:

pushing on the cap of the sample container to strip the sample container from the first and second fingers, and moving the sample container from a first position to a second position within a receptacle during a place operation when the first and second fingers are in an opened configuration.

10. The system of claim 9 further comprising a load limiting device coupled between the robot apparatus and the gripper apparatus, the load limiting device adapted to limit a load applied to the gripper apparatus during a transfer operation.

11. A method of transferring a sample container, comprising:

providing a gripper component including a first moveable jaw and a second moveable jaw each arranged alongside of a gripper axis;

providing a first finger coupled to the first moveable jaw;

providing a second finger coupled to the second moveable jaw;

contacting a cap of the sample container with a seating member moveable along the gripper axis and positioned adjacent to the first and second fingers when the first and second fingers are in an opened configuration;

gripping the sample container with the first finger and the second finger; and performing a place operation wherein a bottom of the sample container is first inserted into a receptacle to a first position within the receptacle using the gripper component, and then the seating member driven by a linear motion-producer contacts the cap of the sample container to move the sample container to a second deeper position within the receptacle.

12. The method of claim 11 further comprising:

performing a pick operation wherein the cap of the sample container is first contacted with the seating member in an extended configuration prior to gripping of the sample container.

13. A gripper apparatus, comprising:

a first gripper component including a first moveable jaw and a second moveable jaw;

a second gripper component including a third moveable jaw and fourth moveable jaw;

a first finger coupled to the first moveable jaw;

a second finger coupled to the second moveable jaw, wherein the first finger and the second finger are each arranged alongside of a gripper axis and are adapted to close by movement of the first moveable jaw towards the second moveable jaw to grip a sample tube body of a sample container;

a third finger coupled to the third moveable jaw;

a fourth finger coupled to the fourth moveable jaw, wherein the third finger and the fourth finger are each arranged alongside of the gripper axis and are adapted to close by movement of the third moveable jaw towards the fourth moveable jaw to grip a cap of a sample container; and a seating member positioned and moveable along the gripper axis, the seating member adapted to contact the cap of the sample container when the first gripper component and the second gripper component are in an opened configuration; and a linear motion-producer coupled to the seating member and configured to provide controlled linear motion to drive the seating member along the gripper axis; and a seating member position controller electrically coupled to the linear motion producer and adapted to drive the seating member to any preprogrammed extension or retraction position alongside the first and second fingers.

14. The gripper apparatus of claim 13, wherein the linear motion-producer is further configured to cause the seating member to push on the cap of the sample container to strip the sample container from the first and second fingers, and wherein the linear motion-producer is further configured to cause the seating member to move the sample container from a first position to a second position within a receptacle during a place operation when the first and second fingers are in an opened configuration.

15. The gripper apparatus of claim 13 wherein the seating member is both extendible and retractable.

16. The gripper apparatus of claim 13, wherein the first finger and the second finger are positioned in an opposed orientation across the gripper axis, the first and second fingers are coupled to a first gripper component including first and second moveable jaws configured to be actuated to open and close the first and second fingers.

17. The gripper apparatus of claim 13, wherein the third and fourth fingers comprise a second pair of fingers which are each shorter in length than a first pair of fingers formed of the first and second fingers.

18. The gripper apparatus of claim 13, further comprising a portion of each of the third and fourth fingers received within recesses formed in the first and second fingers.

19. A sample container transfer system, comprising:

a robot apparatus adapted to be moveable in at least one coordinate direction; and a gripper apparatus coupled to and adapted to be moved by the robot apparatus, the gripper apparatus including a first gripper component including a first moveable jaw and a second moveable jaw each arranged alongside of a gripper axis, a second gripper component including a third moveable jaw and a fourth moveable jaw arranged alongside of the gripper axis, a first finger coupled to the first moveable jaw, a second finger coupled to the second moveable jaw, wherein the first finger and second finger are adapted to close by movement of the first moveable jaw towards the second moveable jaw to grip a sample tube body of a sample container, a third finger coupled to the third moveable jaw, and a fourth finger coupled to the fourth moveable jaw, wherein the third finger and the fourth finger are adapted to close by movement of the third moveable jaw towards the fourth moveable jaw to grip a cap of a sample container; and a seating member positioned and moveable along the gripper axis, the seating member adapted to contact the cap of the sample container when the first gripper component and the second gripper component are in an opened configuration; and a linear motion-producer coupled to the seating member and configured to provide controlled linear motion to drive the seating member along the gripper axis; and a seating member position controller electrically coupled to the linear motion producer and adapted to drive the seating member to any preprogrammed extension or retraction position alongside the first and second fingers to do at least one of:

pushing on the cap of the sample container to strip the sample container from the first and second gripper components, and moving the sample container from a first position to a second position within the receptacle during a place operating when the first and second gripper components are in an opened configuration.

20. A method of transferring a sample container, comprising:
- gripping a sample tube body of the sample container with a first pair of fingers of a gripper apparatus;
- gripping the cap of the sample container with a second pair of fingers of the gripper apparatus;
- transferring the sample container being gripped by the gripper apparatus from a first location to a second location;
- performing a place operation wherein a bottom of the sample container is first inserted into a receptacle to a first position within the receptacle using the gripper apparatus; and
- driving a seating member with a linear motion-producer to contact the cap of the sample container to move the sample container to a second deeper position within the receptacle.

21. The method of claim 20, further comprising:
contacting the cap of the sample container with the seating member during a pick operation.

* * * * *